US012649926B2

(12) United States Patent
Niu et al.

(10) Patent No.: US 12,649,926 B2
(45) Date of Patent: Jun. 9, 2026

(54) **USE OF MfERF026 GENE REGULATION IN GROWTH, DEVELOPMENT, AND STRESS TOLERANCE OF *MEDICAGO SATIVA***

(71) Applicant: Inner Mongolia University, Hohhot City (CN)

(72) Inventors: Yiding Niu, Hohhot City (CN); Jiabin Fu, Hohhot City (CN); Jinfeng Hao, Hohhot City (CN); Yu Wang, Hohhot City (CN)

(73) Assignee: Inner Mongolia University, Hohhot City (CN)

( * ) Notice: Subject to any disclaimer, the term of this patent is extended or adjusted under 35 U.S.C. 154(b) by 0 days.

(21) Appl. No.: 18/651,582

(22) Filed: Apr. 30, 2024

(65) Prior Publication Data

US 2025/0027100 A1     Jan. 23, 2025

(30) Foreign Application Priority Data

Jul. 21, 2023    (CN) ......................... 202310897060.7

(51) Int. Cl.
*C12N 15/82*          (2006.01)

(52) U.S. Cl.
CPC ..... *C12N 15/8218* (2013.01); *C12N 15/8205* (2013.01); *C12N 15/8262* (2013.01); *C12N 2310/14* (2013.01)

(58) Field of Classification Search
None
See application file for complete search history.

(56) References Cited

U.S. PATENT DOCUMENTS

2014/0356961 A1* 12/2014 Meyers .............. C12N 15/8279
435/468

OTHER PUBLICATIONS

Hilty et al., Plant growth: the What, the How, and the Why, 2021, New Phytologist, 232:25-41 (Year: 2021).*
Zhuo et al., A cold responsive ethylene responsive factor from Medicago falcata confers cold tolerance by up-regulation of polyamine turnover, antioxidant protection, and proline accumulation, 2018, Plant Cell Environ, 41:2021-2032 (Year: 2018).*
GenBank Accession No. EX525415 (Year: 2007).*

* cited by examiner

*Primary Examiner* — Bratislav Stankovic
*Assistant Examiner* — Jay Chatterjee
(74) *Attorney, Agent, or Firm* — Berkeley Law & Technology Group, LLP

(57) ABSTRACT

Provided is use of MfERF026 regulation in growth, development, and stress tolerance of *Medicago sativa*, which belongs to the technical field of plant genetic engineering. Provided is use of a regulatory agent for MfERF026, which is an ethylene responsive factor (ERF) in *Medicago falcata*, in promoting growth and development and improving drought tolerance and cold tolerance of *M. sativa*. The inhibited expression of MfERF026, the ERF in *M. falcata* may enhance the drought tolerance and cold tolerance of the *M. sativa*. Moreover, the inhibited expression of MfERF026, the ERF in *M. falcata*, may regulate the growth and development of *M. sativa*, thereby accelerating the growth rate of *M. sativa* to increase the number of leaves. The inhibited expression of MfERF026 provides a novel theoretical basis and a candidate gene for cultivating novel leguminous forage varieties with high resistance, yield, and protein content.

8 Claims, 25 Drawing Sheets

Specification includes a Sequence Listing.

NaCl MfERF026-stem

NaCl MfERF026- leaf

Statics of leaflet width at day 30

Statics of leaflet aspect ratio at day 30

WT

MfERF026 RNAi#16

MfERF026 RNAi#17

MfERF026 RNAi#26

MfERF026 RNAi#29

Superoxide dismutase (SOD) activity determination

*MfERF026* cold stress survival rate

*MfERF026* cold stress electric conductivity

USE OF MfERF026 GENE REGULATION IN GROWTH, DEVELOPMENT, AND STRESS TOLERANCE OF *MEDICAGO SATIVA*

CROSS REFERENCE TO RELATED APPLICATION

This patent application claims the benefit and priority of Chinese Patent Application No. 202310897060.7 filed with the China National Intellectual Property Administration on Jul. 21, 2023, the disclosure of which is incorporated by reference herein in its entirety as part of the present application.

REFERENCE TO SEQUENCE LISTING

A computer readable XML file entitled "GWP20231209446_seqlist", that was created on Jun. 25, 2024, with a file size of about 24,355 bytes, contains the sequence listing for this application, has been filed with this application, and is hereby incorporated by reference in its entirety.

TECHNICAL FIELD

The present disclosure belongs to the technical field of plant genetic engineering, and specifically relates to use of MfERF026 regulation in growth, development, and stress tolerance of *Medicago sativa*.

BACKGROUND

Transcription factors (TFs), also known as trans-acting factors, are DNA-binding proteins that can specifically interact with cis-acting elements in eukaryotic gene promoter regions. The transcription of target genes is activated or inhibited through interactions of the TFs with the cis-acting elements and with other related proteins. In recent years, a series of transcription factors have been isolated from higher plants for regulating the expression of genes related to drought, low temperature, high salt concentration, hormones, pathogen response, and development. APETALA2/ ethylene response element-binding proteins (AP2/EREBPs) are a large family of TFs that are widely present in plants, and their members play important regulatory roles in growth and development, organ construction, adversity stress, and hormone signal response of the plants.

*Medicago sativa* L. is one of the most widely planted artificial pastures in China due to high protein content and rich variety of vitamins, and prepared feed based on same is loved by various livestock because of excellent taste. Therefore, the cultivation of *M. sativa* exhibits a long-term significance for the sustainable development of economy, environment, and agriculture. However, long-term drought conditions generally cause adverse effects on the growth of *M. sativa*, thereby reducing the survival rate and affecting the yield of *M. sativa*.

There is currently a lack of technology for improving novel *M. sativa* varieties. Improving the drought resistance and increasing the growth rate of *M. sativa* through technological means such as molecular genetics and gene editing may greatly promote the application of *M. sativa* in production. However, there is a lack of technology on achieving the drought tolerance in *M. sativa*.

SUMMARY

In view of the deficiencies in the prior art, an objective of the present disclosure is to provide use of a regulatory agent for MfERF026, an ethylene responsive factor (ERF) of *Medicago falcata*, in promoting growth and development and improving drought tolerance and cold tolerance of *M. sativa*.

The objective of the present disclosure is achieved by the following technical solutions:

The present disclosure provides use of a regulatory agent for MfERF026, an ERF of *M. falcata*, in one or more of promoting growth and development and improving drought tolerance and cold tolerance of *M. sativa*, where MfERF026 encodes a protein including any one of the following A1 to A4:

A1, a protein with the amino acid sequence of SEQ ID NO: 2;

A2, a protein that is obtained by substituting and/or deleting and/or adding one or more amino acid residues of A1 and has a same function as that of A1;

A3, a protein that has more than 80% identity with the amino acid sequence defined by A1 or A2 and has a same function as that of A1 or A2; and A4, a fusion protein obtained by ligating a protein tag to an N-terminal and/or a C-terminal on any one of the proteins defined in A1 to A3.

In some embodiments, MfERF026 has the nucleotide sequence of SEQ ID NO: 1.

In some embodiments, the regulatory agent includes an agent that silences or reduces expression of MfERF026.

In some embodiments, the agent that reduces the expression of MfERF026 includes an interfering RNA for the expression of MfERF026.

The present disclosure further provides a trans-acting small interfering RNA (tasiRNA), where the tasiRNA has the nucleotide sequence of SEQ ID NO: 18.

The present disclosure further provides a base fragment for reducing MfERF026 expression obtained based on the tasiRNA, where the base fragment has the nucleotide sequence of SEQ ID NO: 17.

The present disclosure further provides a primer pair for amplifying the base fragment, where the primer pair includes an upstream primer MfERF026 RNAi-F and a downstream primer MfERF026 RNAi-R; the upstream primer MfERF026 RNAi-F has the nucleotide sequence of SEQ ID NO: 14; and the downstream primer MfERF026 RNAi-R has the nucleotide sequence of SEQ ID NO: 15.

The present disclosure further provides an expression vector for reducing MfERF026 expression, where the expression vector includes the base fragment.

The present disclosure further provides an engineering bacterium constructed based on the expression vector.

The present disclosure provides a method for constructing a transgenic *M. sativa*, including the following steps:

infecting a *M. sativa* leaf with the engineering bacterium to obtain a transformed *M. sativa* leaf; and subjecting the transformed *M. sativa* leaf to tissue culture to obtain a transgenic *M. sativa* with inhibited MfERF026 expression.

The embodiments of the present disclosure has following beneficial effects:

The present disclosure provides use of a regulatory agent for MfERF026, an ERF of *M. falcata*, in one or more of promoting growth and development and improving drought tolerance and cold tolerance of *M. sativa*, where MfERF026 encodes a protein including any one of the following A1 to A4: A1, a protein with the amino acid sequence of SEQ ID NO: 2; A2, a protein that is obtained by substituting and/or deleting and/or adding one or more amino acid residues of A1 and has a same function as that of A1; A3, a protein that has more than 80% identity with the amino acid sequence defined by A1 or A2 and has a same function as that of A1 or A2; and A4, a fusion protein obtained by ligating a protein tag to an N-terminal and/or a C-terminal on any one of the proteins defined in A1 to A3.

In the present disclosure, the expression vector that inhibits the expression of MfERF026 is integrated into a *M. sativa* genome using transgenic technology to initially change development, drought resistance, and cold tolerance of the *M. sativa*.

In the present disclosure, the inhibited expression of MfERF026, an ERF of *M. falcata*, in the *M. sativa* may enhance the drought tolerance of the *M. sativa*. Inhibiting the expression of MfERF026 may improve the survival rate of *M. sativa* under drought conditions, reduce the degree of cell membrane damage of *M. sativa* under drought conditions to be maintained at normal levels, thereby improving the drought resistance of *M. sativa*. The inhibited expression of MfERF026, an ERF of *M. falcata*, in the *M. sativa* may enhance the cold tolerance of the *M. sativa*. Inhibiting the expression of MfERF026 may improve the survival rate of *M. sativa* at −7° C. to −8° C. and reduce damages to the cell membrane of *M. sativa* at −7° C. to −8° C., thus improving the cold tolerance of *M. sativa*. The inhibited expression of the ERF gene of *M. falcata* in *M. sativa* may promote the growth and development of *M. sativa*, thereby accelerating the growth and/or increasing the number of *M. sativa* leaves. Inhibiting the expression of MfERF026 in *M. sativa* may regulate the growth of *M. sativa*. Inhibiting the expression of MfERF026 in *M. sativa* may accelerate the growth of *M. sativa* and increase the number of *M. sativa* leaves. In summary, the inhibited expression of MfERF026 increases plant heights, number of tillers, and number of three-trifoliate leaves of *M. sativa*, enhances drought tolerance and cold tolerance of *M. sativa*, and provides a novel theoretical basis and a candidate gene for cultivating novel leguminous forage varieties with high resistance, yield, and protein content.

BRIEF DESCRIPTION OF THE DRAWINGS

To illustrate the examples of the present disclosure or the technical solutions in the prior art more clearly, the accompanying drawings required in the examples will be briefly described below.

DETAILED DESCRIPTION OF THE EMBODIMENTS

Figure 1A:
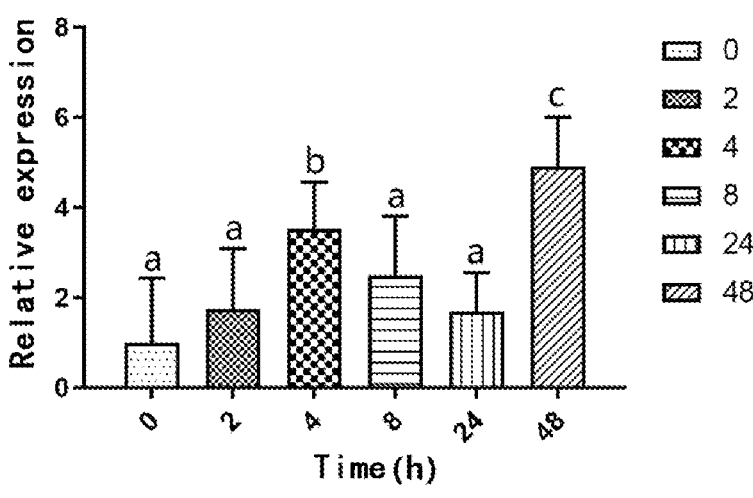
FIGS. 1A-IC show the relative expression of MfERF026 in *M. falcata* under cold stress conditions.

The present disclosure provides use of a regulatory agent for MfERF026, an ERF of *M. falcata*, in one or more of promoting growth and development and improving drought tolerance and cold tolerance of *M. sativa*, where MfERF026 encodes a protein including any one of the following A1 to A4:

A1, a protein with the amino acid sequence of SEQ ID NO: 2;

A2, a protein that is obtained by substituting and/or deleting and/or adding one or more amino acid residues of A1 and has a same function as that of A1;

A3, a protein that has more than 80% identity with the amino acid sequence defined by A1 or A2 and has a same function as that of A1 or A2; and A4, a fusion protein obtained by ligating a protein tag to an N-terminal and/or a C-terminal on any one of the proteins defined in A1 to A3.

In the present disclosure, a protein encoded by MfERF026 has the amino acid sequence of SEQ ID NO: 2, specifically as follows:

```
MNSSTIEQPHNSETKSSSNSSPPPPPSQSLQIKGIRDTSKHPVYRGVRM

RNWGKWVSEIREPKKKSRIWLGTFPTPEMAARAHDVAALSIKGSAAILN

FPELVNLLPRPASLAPRDIQAAATKAAHMEFPSSTASYELTEIIELPRL

GNVGDFGKEFVFMDSIDTSWMFQPPCLQTMEDAIWSDIYNNYS.
```

In the present disclosure, an MfERF026 protein is located in the nucleus; and a C-terminal of the MfERF026 protein has a transcription activation activity.

In the present disclosure, MfERF026 has the nucleotide sequence of SEQ ID NO: 1, specifically as follows:

```
5'-ATGAATAGTAGTACTATTGAACAACCTCATAACTCAGAAACCAAGA

GTAGCTCAAATTCATCACCACCACCACCACCATCACAATCCCTACAAAT

AAAAGGCATAAGAGACACAAGCAAGCATCCAGTATACCGTGGTGTCCGA

ATGCGAAATTGGGGAAAATGGGTGTCCGAAATTCGTGAGCCTAAGAAAA

AATCCCGAATATGGCTCGGCACATTTCCCACACCAGAAATGGCAGCTCG

AGCACACGATGTAGCTGCTCTTAGTATAAAAGGAAGCGCCGCCATTCTC

AACTTCCCTGAGTTAGTAAACTTGCTTCCTCGTCCGGCTTCACTCGCTC

CCCGTGATATTCAAGCAGCCGCTACCAAAGCCGCTCACATGGAGTTTCC

ATCTTCAACAGCTTCATATGAATTGACTGAGATAATTGAGCTTCCTCGT

TTGGGAAACGTTGGAGATTTTGGAAAGGAGTTTGTATTTATGGATTCCA

TTGATACTTCGTGGATGTTTCAGCCTCCTTGCTTGCAAACCATGGAAGA

TGCGATTTGGAGTGACATTTATAATAACTATAGCTAG-3'.
```

In some embodiments, the regulatory agent includes an agent that silences or reduces expression of MfERF026. The agent that reduces the expression of MfERF026 includes preferably an interfering RNA for the expression of MfERF026.

In some embodiments, a process of improving the drought tolerance of *M. sativa* includes: improving the survival rate of *M. sativa* under drought conditions and/or reducing the degree of cell membrane damage of *M. sativa* under drought conditions. The drought tolerance of *M. sativa* can be improved by reducing the expression of MfERF026, thus improving the survival rate of *M. sativa* under drought conditions. This can keep the electrical conductivity of *M. sativa* at a low level under drought conditions and reduce the degree of cell membrane damage of *M. sativa* under drought conditions.

In some embodiments, a process of improving the cold tolerance of *M. sativa* includes: improving the survival rate of *M. sativa* under cold conditions and/or reducing the degree of cell membrane damage of *M. sativa* under cold conditions. Reducing the expression of MfERF026 can improve the survival rate of *M. sativa* at –7° C. to –8° C. and reduce damages to the cell membrane of *M. sativa* at –7° C. to –8° C., thus improving the cold tolerance of *M. sativa.*

In some embodiments, a process of promoting the growth and development of *M. sativa* includes: promoting the growth of *M. sativa* and/or increasing the number of *M. sativa* leaves. The growth of *M. sativa* can be promoted by reducing the expression of MfERF026, thereby increasing the plant height, number of tillers, number of segments, and number of trifoliate leaves of *M. sativa.*

The present disclosure further provides a tasiRNA, where the tasiRNA has the nucleotide sequence of SEQ ID NO: 18: 5'-TTCAGAGGTGAAGACACACGTA-3'.

The present disclosure further provides use of the tasiRNA in inhibiting MfERF026 expression. The tasiRNA can degrade the mRNA of MfERF026, blocking the formation of the MfERF026 protein to complete the inhibited expression of MfERF026. In some embodiments, the tasiRNA is ligated to a target gene fragment and introduced into *M. sativa* to inhibit expression of the target gene. In some embodiments, the tasiRNA is ligated before the 5'-end of the target gene fragment; and the target gene fragment is a sequence of about 300 bp on the 3'-end of the target gene. In addition to reducing the expression of MfERF026, the tasiRNA can also interfere with the expression of other genes.

The present disclosure further provides a base fragment for reducing MfERF026 expression obtained based on the tasiRNA, where the base fragment preferably has the nucleotide sequence of SEQ ID NO: 17. The base fragment has an efficiency of 87% to 99% in inhibiting the expression of MfERF026, showing an obvious inhibitory effect on the expression.

The present disclosure further provides a primer pair for amplifying the base fragment. In some embodiments, the primer pair includes an upstream primer MfERF026 RNAi-F and a downstream primer MfERF026 RNAi-R; the nucleotide sequence of the upstream primer MfERF026 RNAi-F is set forth in SEQ ID NO: 14, specifically: 5'-CGG-GATCCTTCAGAGGTGAAGACACACGTA-GATGTAGCTGCTCTTAGTAT-3'; and the nucleotide sequence of the downstream primer MfERF026 RNAi-R is set forth in SEQ ID NO: 15, specifically: 5'-GCTCTA-GACTAGCTATAGTTATTATAAATG-3'. In some embodiments, the base fragment includes restriction endonuclease sites BamHI and XbaI to facilitate ligation with the expression vector.

In some embodiments, the upstream primer MfERF026 RNAi-F carries the tasiRNA. The base fragment of SEQ ID NO: 17 is preferably obtained M through the MfERF026 RNAi-F and MfERF026 RNAi-R, with the cDNA of *M. falcata* as a template. In some embodiments, the base fragment is a fragment of MfERF026 carrying tasiRNA. The base fragment can reduce the expression of MfERF026.

The present disclosure further provides a preparation for reducing MfERF026 expression, including one or more of an expression cassette, a vector, or a transgenic cell of the base fragment according to the present disclosure.

The present disclosure further provides an expression vector for reducing MfERF026 expression, where the expression vector includes the base fragment. In some embodiments, the expression vector includes a pCAM1307 plasmid.

The present disclosure further provides an engineering bacterium constructed based on the expression vector for reducing MfERF026 expression. In some embodiments, the engineering bacterium includes *Agrobacterium* EHA105.

The present disclosure provides a method for constructing a transgenic *M. sativa,* including the following steps:

infecting a *M. sativa* leaf with the engineering bacterium to obtain a transformed *M. sativa* leaf; and subjecting the transformed *M. sativa* leaf to tissue culture to obtain the transgenic *M. sativa* with inhibited MfERF026 expression.

In some embodiments, a *M. sativa* leaf is infected with the engineering bacterium to obtain a transformed *M. sativa* leaf.

In some embodiments, a process of obtaining the engineering bacterium includes: transforming the expression vector that inhibits MfERF026 expression into the engineering bacterium, and screening a positive engineering bacterium to obtain a target engineering bacterium.

In some embodiments, the expression vector for inhibiting MfERF026 expression includes a recombinant plasmid pCAM1307-RNAi-MfERF026. In some embodiments, the engineering bacterium includes *Agrobacterium* EHA105. There is no particular limitation on a transformation method for transforming *Agrobacterium* with the expression vector, and any conventional transformation method in this field can be used. In some embodiments, the transformation method includes liquid nitrogen quick freezing and heat shock; the liquid nitrogen quick freezing is conducted for preferably 2 min; and the heat shock is conducted for preferably 30 s. After the transformation is completed, a positive colony is preferably selected to obtain positive *Agrobacterium*. A process of selecting the positive colony preferably includes sequentially conducting primary culture and solid culture on resulting transformed *Agrobacterium*. The primary culture is preferably conducted on a YEB medium at 28° C. and 190 rpm for 4 h. After the primary culture is completed, the *Agrobacterium* is preferably subjected to the solid culture. The solid culture is preferably conducted on a YEB solid medium containing kanamycin and rifampicin; the YEB solid medium has the kanamycin of preferably 50 mg/L and the rifampicin of 75 mg/L by mass concentration. The solid culture is preferably conducted at 28° C. for 2 d. The solid culture is preferably conducted by inverted culture. After the solid culture is completed, a colony obtained by screening is a positive colony; and the positive colony is the positive engineering bacterium, referred to as the engineering bacterium for short.

In the present disclosure, the *M. sativa* leaf is infected with the positive engineering bacterium to obtain the transformed *M. sativa* leaf.

In some embodiments, after the positive engineering bacterium is obtained, its positive bacterial colonies are subjected to expanded culture. The expanded culture is preferably conducted in a YEB medium. The expanded culture is conducted at preferably 28° C. In some embodiments, an *Agrobacterium* bacterial solution with an $OD_{600}$ value of 0.6 to 0.8 is obtained through the expanded culture. After the *Agrobacterium* bacterial solution is obtained, the bacterial solution is preferably centrifuged, and a resulting supernatant is discarded to collect positive *Agrobacterium* bacterial cells. The centrifugation is conducted at preferably 2,400 rpm for 15 min. After the positive *Agrobacterium* bacterial cells are obtained, the cells are preferably resuspended to obtain an *Agrobacterium* infection solution. The *Agrobacterium* bacterial cells are preferably resuspended in a SH3α liquid medium containing 100 μmol/L acetosyringone.

In some embodiments, *M. sativa* leaves are infected with the *Agrobacterium* infection solution to obtain transformed *M. sativa* leaves. The *M. sativa* leaves are preferably leaves of Zhongmu No. 1, more preferably leaves in well growth condition after being cultivated for 4 to 6 weeks. The *M. sativa* is preferably transformed by an EHA105-mediated leaf disc method. Before the transformation, the *M. sativa* leaves are preferably washed and sterilized in sequence to obtain pretreated *M. sativa* leaves. The washing is preferably conducted using ultrapure water. After the washing is completed, the sterilization is preferably conducted. The sterilization is preferably conducted using a mixed solution of hypochloric acid rinsing solution and Tween-20. In some embodiments, hypochloric acid in the hypochloric acid rinsing solution has a mass percentage of 7%. The Tween-20 and the hypochloric acid rinsing solution are at a volume ratio of preferably 1:3000. The sterilization is conducted for preferably 10 min to 13 min. After the pretreated *M. sativa* leaves are obtained, the pretreated *M. sativa* leaves and the *Agrobacterium* infection solution are preferably mixed to obtain a *M. sativa* infection system. The *M. sativa* infestation system is preferably vacuum infiltrated. The vacuum infiltration is preferably conducted at 0.08 MPa to 0.09 MPa for 10 min. After the vacuum infiltration is completed, the *Agrobacterium* suspension is preferably discarded, and the

8

*Agrobacterium* on the leaf surface is removed by sucking on sterilized filter paper to obtain transformed *M. sativa* leaves.

In some embodiments, the transformed *M. sativa* leaf is subjected to tissue culture to obtain the transgenic *M. sativa* with inhibited MfERF026 expression.

In some embodiments, the transformed *M. sativa* is dark-cultured on a common medium to obtain a primary culture explant. The dark culture is preferably conducted at 24° C. for 24 h to 30 h. In some embodiments, the primary culture explant is transferred to a selection medium for subculture to obtain a callus. The subculture is conducted at preferably 24° C. for 5 to 6 weeks; and the subculture is preferably conducted once every 2 weeks. The subculture is preferably conducted until the callus is formed. The subculture is preferably completed in the dark.

In some embodiments, the callus is transferred to an MSBK medium for embryoid culture. The embryoid culture is conducted for preferably 10 d to 14 d. The embryoid culture is preferably conducted until a green embryoid appears; and the embryoid culture is preferably conducted under a light intensity of 150 μmol/m²/s at 20° C. to 24° C., with a light-to-dark ratio of 16 h: 8 h. After the embryoid culture is completed, the callus with green embryoid is obtained. In some embodiments, the callus of the green embryoid is cultured for shoot differentiation. The shoot differentiation is preferably conducted in an SH9 medium. The shoot differentiation is conducted under alight intensity of preferably 150 μmol/m²/s at preferably 20° C. to 24° C. with a light-to-dark ratio of 16 h: 8 h for 6 to 8 weeks; and during the shoot differentiation, subculture is preferably conducted once every 3 to 4 weeks. When the shoot differentiation is completed, a trifoliate plant with 2 to 3 fully-expanded leaves is obtained, which is referred to as a trifoliate plant. In some embodiments, the trifoliate plant is subjected to rooting culture to obtain rooted seedlings. The rooting culture is preferably conducted in an MSO medium. The rooting culture is preferably conducted under a light intensity of 150 μmol/m²/s at 20° C. to 24° C. with a light-to-dark ratio of 16 h: 8 h for 1 month. If vigorously growing seedlings are difficult to take root in one month, indole 3-acetic acid (IAA) is preferably added to the MSO medium to promote rooting. The IAA is added at preferably 1 mg/L.

In some embodiments, the rooted seedlings are subjected to acclimatization. The acclimatization is preferably conducted in a soil matrix including vermiculite and perlite at a volume ratio of 1:1. The acclimatization is preferably conducted under a light intensity of 150 μmol/m²/s at 20° C. to 24° C. with a light-to-dark ratio of 16 h: 8 h for 1 to 2 weeks. After the acclimatization is completed, the seedlings are preferably transplanted to a matrix containing nutrient soil and vermiculite at a volume ratio of 1:1 for culture, to obtain the transgenic *M. sativa* with inhibited MfERF026 expression.

In some embodiments, the expression vector that inhibits MfERF026 is integrated into the genome of the transgenic *M. sativa* to initially change the development, drought resistance, and cold resistance of the *M. sativa* in an orientation manner. The inhibited expression of MfERF026 increases plant heights, number of tillers and segments, and number of trifoliate leaves of *M. sativa*, enhances drought tolerance and cold tolerance of *M. sativa*, and provides a novel theoretical basis and a candidate gene for cultivating novel leguminous forage varieties with high anti, yield, and protein content.

In order to further illustrate the present disclosure, the technical solutions provided by the present disclosure are described in detail below in connection with accompanying drawings and examples, but these examples should not be construed to limit the claimed scope of the present disclosure.

In the present disclosure, the media used are as follows:

The minimal medium includes the following components: $MgSO_4 \cdot 7H_2O$ 185 mg/L, $KNO_3$ 2,830 mg/L, $(NH_4)_2 SO_4 \cdot 463$ mg/L, $CaCl_2 \cdot 2H_2O$ 166 mg/L, $KH_2PO_4 \cdot 400$ mg/L, $MnSO_4H_2O$ 10 mg/L, $H_3BO_3$ 5.0 mg/L, $ZnSO_4 \cdot 7H_2O$ 1.0 mg/L, KI 1.0 mg/L, $Na_2MoO_4 \cdot 2H_2O$ 0.1 mg/L, $CuSO_4 \cdot 5H_2O$ 0.2 mg/L, $CoCl_2 \cdot 6H_2O$ 0.1 mg/L, EDTA-FeNa 140 mg/L, thiamine hydrochloride 5.0 mg/L, pyridoxine hydrochloride 5.0 mg/L, nicotinic acid 5.0 mg/L, and inositol 100 mg/L; and the minimal medium has a pH value of 5.8 to 6.0.

In addition to the minimal medium, the co-culture medium further consists of: sucrose 30 g/L, acetosyringone 100 μmol/L, 2,4-D 4 mg/L, 6-BA 0.5 mg/L, and phytagel 3 g/L.

In addition to the minimal medium, the callus medium (subculture medium) further consists of: sucrose 30 g/L, 2,4-D 4 mg/L, 6-BA 0.5 mg/L, timentin 200 mg/L, hygromycin B 10 mg/L, and phytagel 3 g/L.

The embryoid induction medium (MSBK medium) uses MS medium as the minimal medium and further consists of: sucrose 30 g/L, kinetin 1 mg/L, 6-BA 0.5 mg/L, timentin 150 mg/L, hygromycin B 5 mg/L, and phytagel 3 g/L, pH=5.8-6.0.

In addition to the minimal medium, the embryoid differentiation medium (SH9 medium) further consists of: sucrose 20 g/L, timentin 150 mg/L, hygromycin B 5 mg/L, and phytagel 3 g/L, pH=5.8-6.0.

The rooting medium uses MS medium as the minimal medium and further consists of: 10 g/L sucrose and 3 g/L phytagel, pH=5.8-6.0.

SH3α medium includes the following components: N6 macroelement 100 mL; SH trace salt 1 mL; SH vitamin 1 mL; inositol 100 mg; sucrose 30 g; 10 mg/mL 2,4-D 0.4 mL; 1 mg/mL 6-BA 0.5 mL; 100 mM acetosyringone (AS) 1 mL; 400 mg/mL TMT 0.5 mL; 50 mg/mL hygromycin (Hyg) 200 μL; phytagel 3 g, adding water to 1 L; pH=5.8.

N6 macroelement: $MgSO_4 \cdot 7H_2O$ 1.85 g/L, $KNO_3$ 28.3 g/L, $(NH_4)_2SO_4 \cdot 4.63$ g/L, $CaCl_2 \cdot 2H_2O$ 2.475 g/L, and $KH_2PO_4 \cdot 4$ g/L.

SH trace salt: $MnSO_4H_2O$ 1 g/L, $H_3BO_3$ 0.5 g, $ZnSO_4 \cdot 7H_2O$ 0.1 g, KI 0.1 g, $Na_2MoO_4 \cdot 2H_2O$ 0.01 g, and $H_2O$ 100 mL.

SH vitamin: nicotinic acid 0.5 g, thiamine hydrochloride B1 0.5 g, pyridoxine hydrochloride B6 0.5 g, and $H_2O$ 100 mL.

Example 1

Obtaining the MfERF026 Transcription Factor from *M. falcata*

The total RNA was extracted from the stem tissue of wild-type *M. falcata* plants treated with 250 mmol/L NaCl stress for 24 h.

The total RNA was extracted using the liquid nitrogen grinding method and Trizol RNA extraction reagent from Takara Biotech.

cDNA synthesis: the cDNA was synthesized by reverse transcription according to the instructions of Takara Biotech's reverse transcription kit (6210A).

Real-time quantitative polymerase chain reaction (RT-qPCR) was conducted using MfERF026-F and MfERF026-R as primers according to the instructions of PrimeSTAR® GXL DNA Polymerase Kit (TAKARA, Code No. R050A), with primer information shown in Table 1.

TABLE 1

| Primers for amplifying MfERF026 | | |
| --- | --- | --- |
| Primer name | Primer ID | 5'-3' |
| MfERF026-F | SEQ ID NO: 3 | TTTATTTCTCTCCTTCCCAT |
| MfERF026-R | SEQ ID NO: 4 | AAACACACTAAGACATTCACA |

Polymerase chain reaction (PCR) conditions included: initial denaturation at 95° C. for 5 min; denaturation at 98° C. for 10 s; annealing at 51° C. for 30 s; extension at 68° C. for 1 min, 30 cycles; post-extension at 68° C. for 10 min; and storage at 4° C.

After the PCR was completed, a target fragment (about 700 bp) was recovered using a SanPrep column DNA gel recovery kit of Sangon Biotech Co., Ltd., and the operations were done according to the instructions of the kit.

The recovered target fragment was sequenced, and the sequencing results were compared to obtain the coding sequence (CDS) of MfERF026 of *M. falcata*. The CDS of MfERF026 had the nucleotide sequence of SEQ ID NO: 1 and the amino acid sequence of SEQ ID NO: 2.

Example 2

Analysis of Expression Pattern of MfERF026 n *M. falcata*

The plant material was wild-type *M. falcata* that had grown normally for 30 d.

4° C. cold stress treatment: the *M. falcata* was placed in a 4° C. plant low-temperature incubator to allow stress treatment for 0 h, 2 h, 4 h, 8 h, 24 h, and 48 h separately.

Salt stress treatment: the *M. falcata* was placed in a 250 mM NaCl solution to allow stress treatment for 0 h, 2 h, 4 h, 8 h, 24 h, and 48 h separately.

Drought stress treatment: the *M. falcata* was placed in a 100 mM mannitol solution to allow stress treatment for 0 h, 2 h, 4 h, 8 h, 24 h, and 48 h separately.

ABA stress treatment: the *M. falcata* was placed in a 100 μM ABA solution to allow stress treatment for 0 h, 2 h, 4 h, 8 h, 24 h, and 48 h separately.

The root, stem, and leaf tissues of *M. falcata* were separated at different stress time points, wrapped in tin foil, labeled (stress conditions, stress time, and tissue type), snap-frozen in liquid nitrogen and stored at −80° C.

RNA was extracted from *M. falcata* under the above stress treatment conditions, and complementary DNA (cDNA) was obtained through reverse transcription. RT-qPCR was conducted using the cDNA as a template and MfERF026 DL-F and MfERF026 DL-R as primers according to the instructions of a TAKARA Biotechnology Fluorescence Quantitative Kit (RR047Q). At the same time, a glyceraldehyde-3-phosphate dehydrogenase (GAPDH) gene (GenBank accession number: GQ398120) was used as a reference gene for the quantitative polymerase chain reaction (Q-PCR). The primer sequences of MfERF026 DL-F, MfERF026 DL-R, and reference gene are shown in Table

TABLE 2

| Primer information | | |
|---|---|---|
| Primer name | Primer ID | 5'-3' |
| MfERF026DL-F | SEQ ID NO: 5 | ATTCAAGCAGCCGCTACCAA |
| MfERF026DL-R | SEQ ID NO: 6 | CCTTTCCAAAATCTCCAACG |
| Actin-F | SEQ ID NO: 19 | GCTGATAGGATGAGCAAGGAG |
| Actin-R | SEQ ID NO: 20 | GAGCCTCCAATCCAGCAGACACTAT |

The relative expression level of MfERF026 was calculated based on the RT-qPCR results using a $2^{-\Delta\Delta Ct}$ method.

Figure 1B:
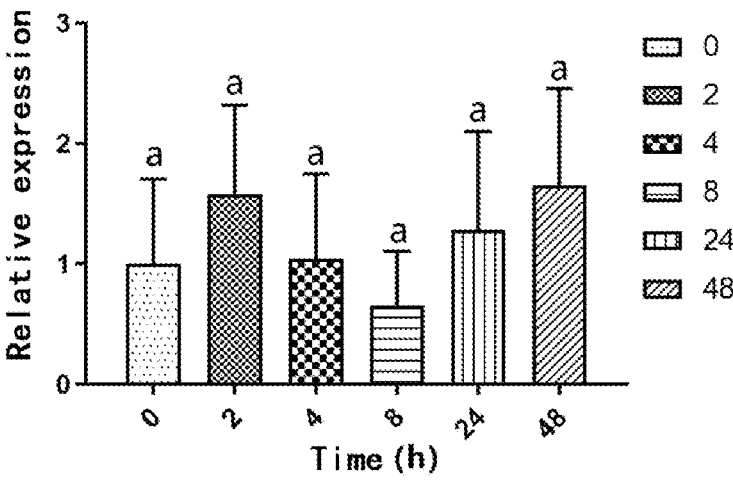
Figure 1C:
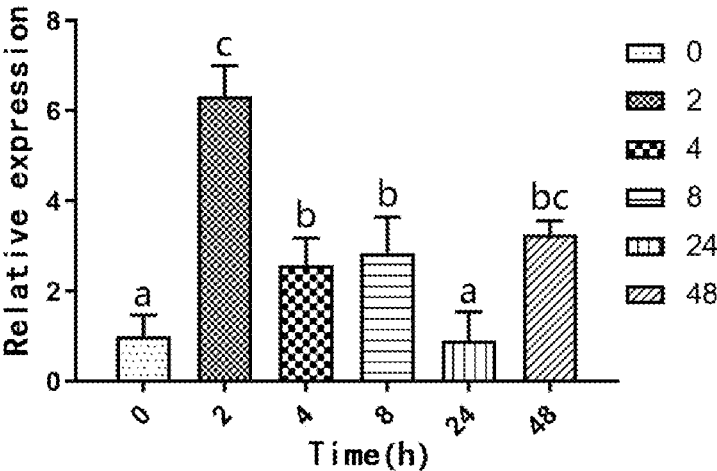
Figure 2A:
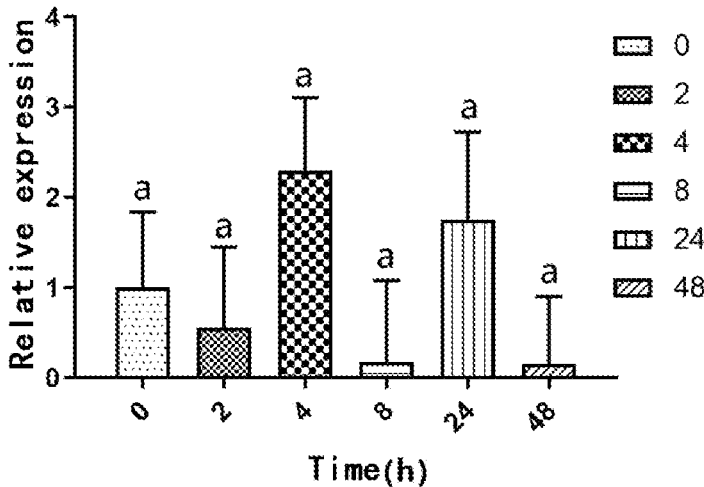
FIGS. 2A-2C show the relative expression of MfERF026 in *M. falcata* under salt stress conditions.
Figure 2B:
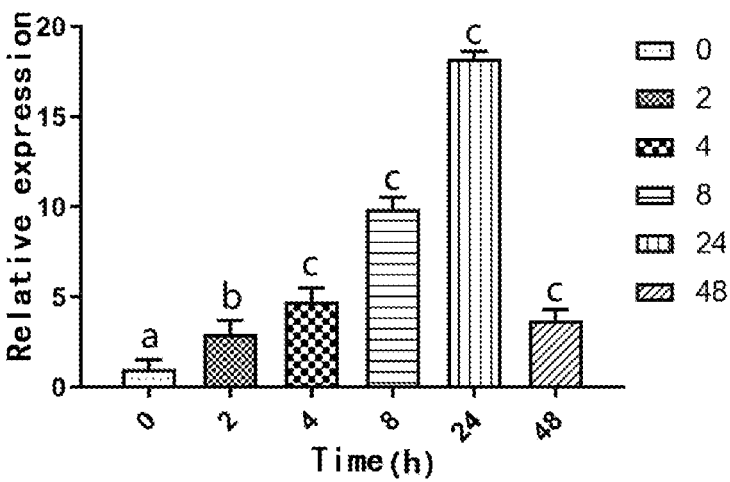
Figure 2C:
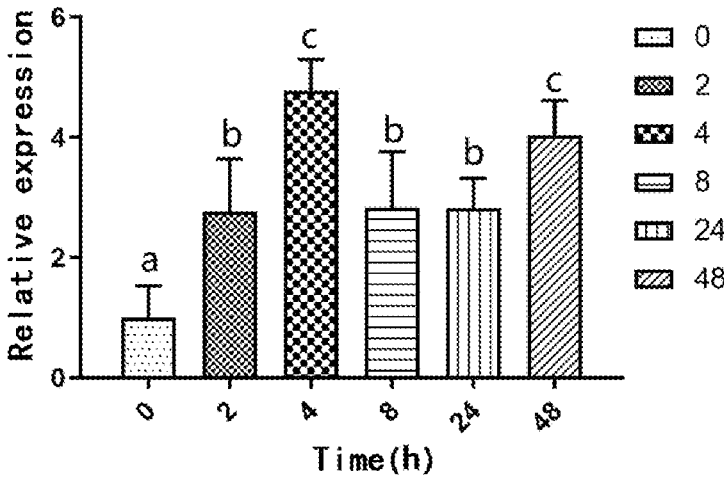
Figure 3A:
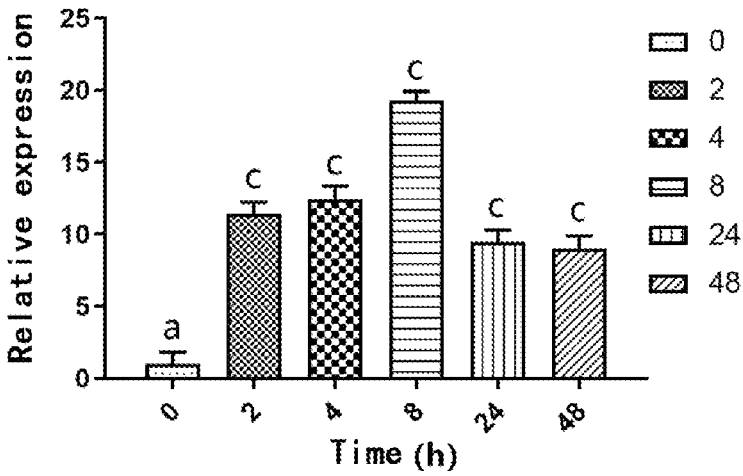
FIGS. 3A-3C show the relative expression of MfERF026 in *M. falcata* under drought stress conditions.
Figure 3B:
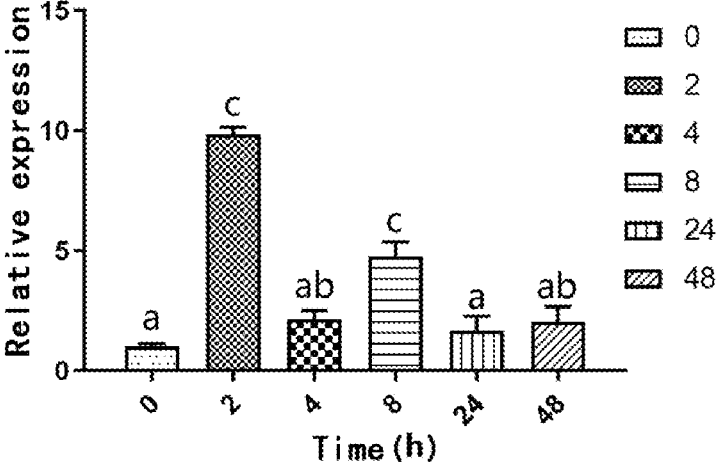
Figure 3C:
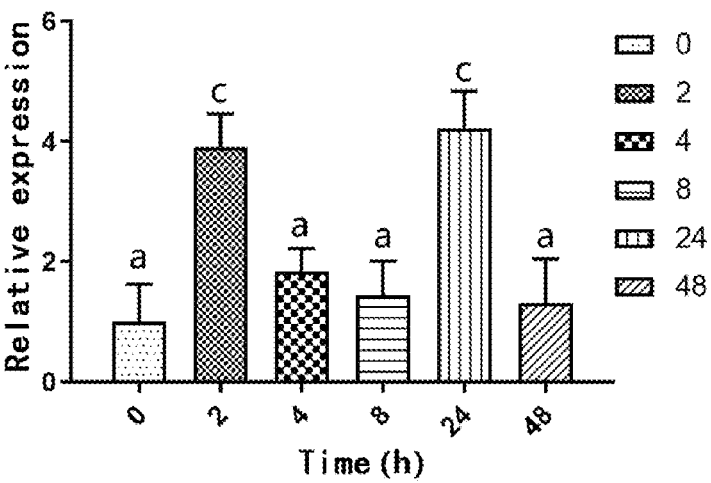
Figure 4A:
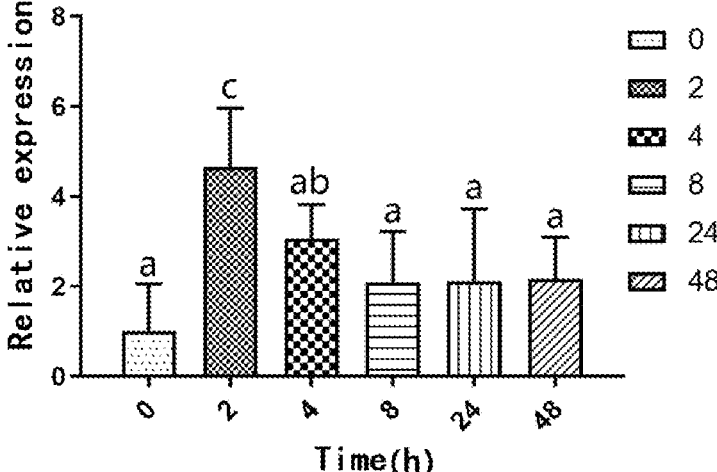
FIGS. 4A-4C show the relative expression of MfERF026 in *M. falcata* under abscisic acid (ABA) stress conditions.
Figure 4B:
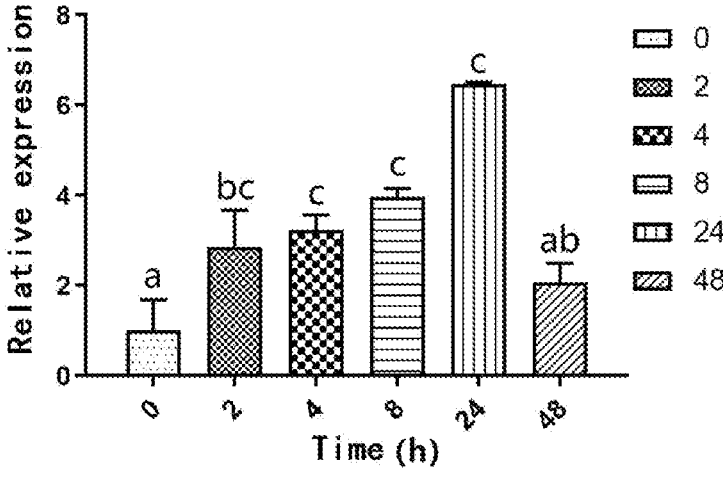
Figure 4C:
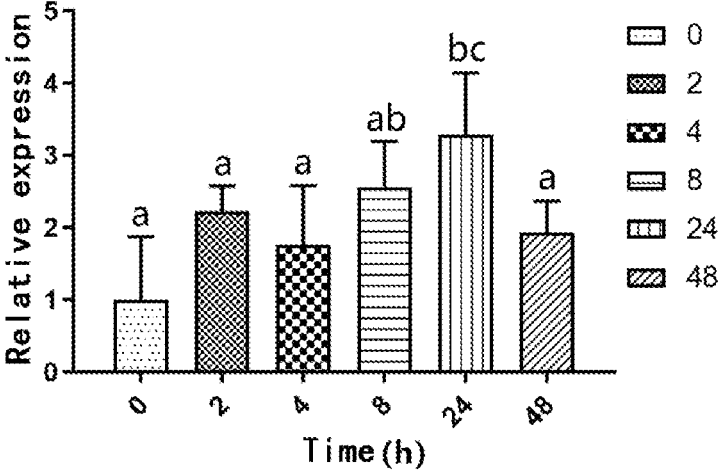

FIGS. 1A-1C show the relative expression of MfERF026 under cold stress conditions obtained by RT-qPCR. FIGS. 2A-2C shows the relative expression of MfERF026 under salt stress conditions obtained by RT-qPCR. FIGS. 3A-3C shows the relative expression of MfERF026 under drought stress conditions obtained by RT-qPCR. FIGS. 4A-4C shows the relative expression of MfERF026 under ABA stress conditions obtained by RT-qPCR.

As shown in FIG. 1A to FIG. 4C, MfERF026 was highly expressed under low temperature, salt, drought, and ABA treatments. The expression level reached maximum under drought stress, indicating a significant response to osmotic stress. The expression levels in plant roots, stems, and leaves were different, and their expression levels increased or decreased significantly with time. These results proved that MfERF026 responded to the low temperature, salt, drought, and ABA treatments.

Example 3

Analysis of Subcellular Localization of MfERF026 in *M. falcata*

1. Construction of Recombinant Plasmid pBE-GFP-MfERF026

The *M. falcata* cDNA was obtained using the method in Example 1.

The MfERF026 cDNA was ligated into a pEASY®-Blunt vector according to the instructions of a pEASY®-Blunt kit (CB101-01) of TransGen Biotech.

PCR was conducted using a primer pair of MfERF026 PBE-F and MfERF026 PBE-R to obtain the full-length cDNA of MfERF026 with BamHI and SalI restriction sites. The primer sequences for the primer pair of MfERF026 PBE-F and MfERF026 PBE-R are shown in Table 3.

TABLE 3

| Primer information for MfERF026 PBE-F and MfERF026 PBE-R | | |
|---|---|---|
| Primer name | Primer ID | 5'-3' |
| MfERF026 PBE-F | SEQ ID NO: 7 | GACTCTAGAGCAGTCGACGATGAATAGTAGTACTATTGAAC |
| MfERF026 PBE-R | SEQ ID NO: 8 | GGCGACCGGTGGATCCCGGCTATAGTTATTATAAATGTCAC |

The PCR system is shown in Table 4.

TABLE 4

| PCR system | |
|---|---|
| Reagent | Consumption (μL) |
| 5xPrime STAR GXL Buffer | 10.0 |
| dNTP Mixture (2.5 mmol/L) | 4.0 |
| MfERF026 PBE-F(5 μmoL) | 2.0 |
| MfERF026 PBE-R(5 μmoL) | 2.0 |
| Prime STAR GXL DNA Ploymerase | 1.0 |
| pEASY ®-Blunt-MfERF026 (100 ng/μL) | 1.0 |
| ddH₂O | Supplementing to 50.0 μL |

PCR conditions included: initial denaturation at 98° C. for 5 min; denaturation at 98° C. for 10 s; annealing at 60° C. for 30; extension at 68° C. for 1 mo, 30 cycles; post-extension at 68° C. for 10 min; and storage at 4 (C.

After the PCR was completed, agarose gel electrophoresis was conducted to detect the PCR products, and a target fragment was obtained by determining the size of the band.

After the PCR was completed, a target fragment (about 470 bp) of MERF026 was recovered using a SanPrep column DNA gel recovery kit of Sangon Biotech Co., Ltd. according to the instructions of the kit.

A pBE empty plasmid was double-digested with BamHI and SalI using an enzyme digestion system shown in Table 5.

TABLE 5

| Enzyme digestion system | |
|---|---|
| Reagent | Consumption (μL) |
| pBE plasmid (100 ng/μL) | 10 |
| 10xT Buffer | 3 |
| BcmH I | 1 |
| Sal I | 1 |
| ddH₂O | Supplementing to 20 μL |

The enzyme digestion system was mixed for digestion at 37° C. for 1 h. After the enzyme digestion, a resulting linearized plasmid vector was recovered using the SanPrep column DNA gel recovery kit of Sangon Biotech Co., Ltd. according to the instructions of the kit.

The homologous recombination ligation of the target fragment and the pBE vector was conducted using TaKaRa In-Fusion® HD Cloning Kit. An obtained ligation product was transformed into *E. coli* DH5a, tested by colony PCR, and sent for sequencing. The obtained positive clones verified by sequencing were subjected to expanded culture, and plasmids were extracted for later use.

2. Transformation of *Agrobacterium* GV3101 with Recombinant Plasmid pBE-GFP-MfERF026

5 μL of the recombinant plasmid pBE-GFP-MfERF026 at a concentration of 100 ng/μL and empty pBE-GFP were added to 50 μL of *Agrobacterium* GV3101 competent cells. After gently mixing, the cells were placed on ice for 5 min, in liquid nitrogen for 5 min, transferred to a 37° C. water bath for heat shock for 5 min, and then in ice water bath for 5 min. The cells were added to 700 μL of LB liquid medium balanced to room temperature on a clean workbench, and cultured at 28° C. and 200 rpm for 2 h.

After the culture was completed, the cells were centrifuged at 6,000 rpm for 1 min, 500 μL of the supernatant was discarded, and the remaining liquid was pipetted to resuspend the cells and facilitate spreading in the next step. 80 μL of the remaining liquid was spread on LB solid medium containing 50 mg/L Kan (kanamycin), 50 mg/L genta (gentamicin), and 25 mg/L Rif (rifampicin antibiotic), and then incubated upside down at 28° C. for 36 h to 48 h until a single colony grew.

lower epidermis of 4-week-old tobacco leaves, and cultured in a plant tissue culture lab for 36 h.

4. Observation of Leaf Fluorescence with Laser Confocal Microscope

The tobacco leaves were cut at the infected site and placed in a petri dish, DAPI was added dropwise on the leaves to allow staining for 20 min, and washed twice with PBS for 20 min each time. The stained leaves were placed face up on a glass slide and observed with a laser confocal microscope.

Figure 5:
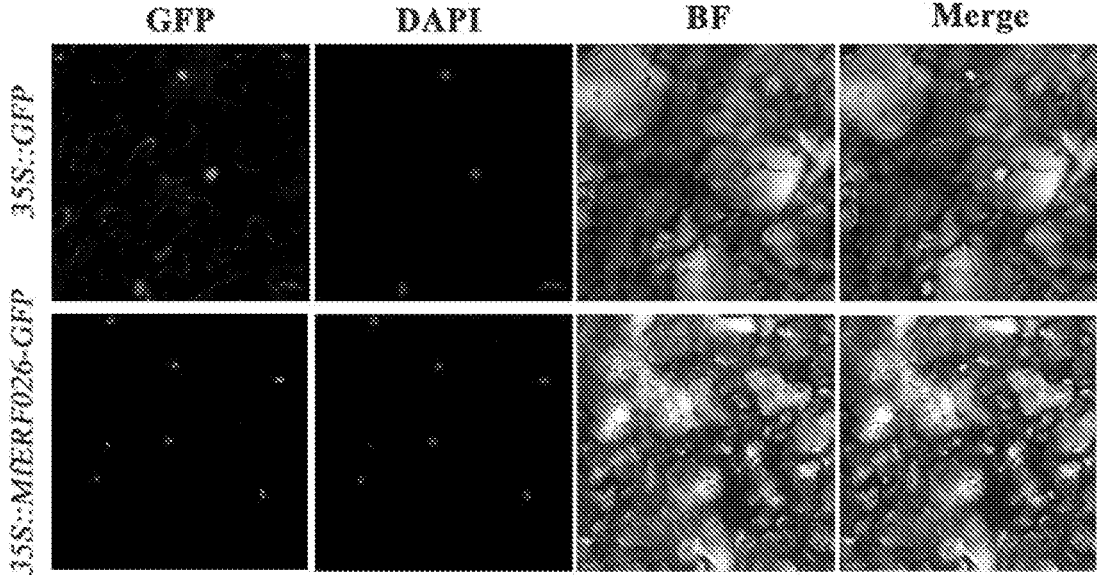
FIG. 5 shows the observation results under a laser confocal microscope in the subcellular localization experiment of MfERF026 protein.

FIG. 5 shows the observation results under a laser confocal microscope in the subcellular localization experiment.

As shown in FIG. 5, the fluorescence signal of GFP fused to MfERF026 co-localized with the DAPI, indicating that MfERF026 was located in the nucleus.

Example 4

Analysis of Transcriptional Activation Experiment of MfERF026 n *M. falcata*

The *M. falcata* cDNA was obtained using the method in Example 1.

The cDNA of MfERF026 was ligated into a pEASY®-Blunt vector according to the instructions of a pEASY®-Blunt kit (CB101-01) of TransGen Biotech.

5 fragments of MfERF026 were obtained using different primers, and included: full length (a), N-terminal+ERF domain (b), ERF domain (c), ERF domain+C-terminal (d), and C-terminal (e), and primer information is shown in Table 6.

TABLE 6

Primer encoding 5 fragments of MfERF026: full length, N-terminal + ERF domain, ERF domain, ERF domain + C-terminal, and C-terminal

| Target fragment | Primer name | Primer ID | 5'-3' |
|---|---|---|---|
| MfERF026-a | MfERF026a-F | SEQ ID NO: 9 | CGGGATCCATGAATAGTAGTACTATTGAAC |
| | MfERF026a-R | SEQ ID NO: 10 | ATAAGAATGCGGCCGCCTAGCTATAGTTATTATAAATG |
| MfERF026-b | MfERF026a-F | SEQ ID NO: 9 | CGGGATCCATGAATAGTAGTACTATTGAAC |
| | MfERF026b-R | SEQ ID NO: 11 | ATAAGAATGCGGCCGCAAGCAAGTTTACTAACTCAG |
| MfERF026-c | MfERF026c-F | SEQ ID NO: 12 | CGGGATCCGTATACCGTGGTGTCCG |
| | MfERF026b-R | SEQ ID NO: 11 | ATAAGAATGCGGCCGCAAGCAAGTTTACTAACTCAG |
| MfERF026-d | MfERF026c-F | SEQ ID NO: 12 | CGGGATCCGTATACCGTGGTGTCCG |
| | MfERF026a-R | SEQ ID NO: 10 | ATAAGAATGCGGCCGCCTAGCTATAGTTATTATAAATG |
| MfERF026-e | MfERF026e-F | SEQ ID NO: 13 | CGGGATCCCCTCGTCCGGCTTCACTC |
| | MfERF026a-R | SEQ ID NO: 10 | ATAAGAATGCGGCCGCCTAGCTATAGTTATTATAAATG |

3. Injection into the Lower Epidermis of Nicotiana *Benthamiana* Leaves

A single colony of positive *Agrobacterium* GV3101 was picked in YEB liquid medium containing Kan, Gent, and Rif, and cultured with shaking at 28° C. for 24 h.

After the culture was completed, 500 μL of the bacterial solution was added into 40 mL of triple antibody (Kan, Gent, and Rif)-containing YEB liquid medium containing 500 μL of 1 M 2-(N-morphine)ethanesulfonic acid (MES) and 5 μL of 200 mM acetosyringone (AS, which facilitated *Agrobacterium* infection of tobacco leaves), and cultured with shaking at 28° C. until the OD$_{600}$ value was at 1.2 to 1.5.

Figure 6A:
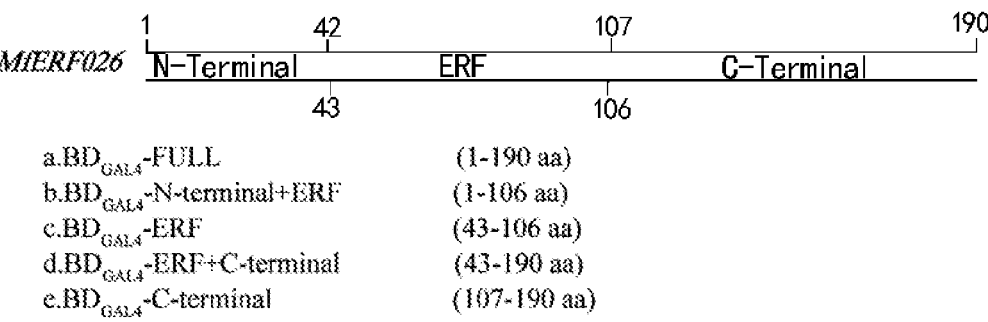
FIGS. 6A-6B show the culture results of yeast transformants using fusion expression vectors of 5 different target fragments of MfERF026 in a transcription activation experiment on different media.

After the culture was completed, the cells were collected by centrifugation (4° C., 8,000 rpm, 10 min), added with an infection solution (where each 100 mL of ddH$_2$O included 1 mL of 1 M MES, 1 mL of 1 M MgCl$_2$, and 100 μL of 200 mM AS), resuspended until the OD$_{600}$ value was 1.0, allowed to stand in the dark for 4 h, then injected into the PCR was conducted using the primers shown in Table 6 separately to obtain the 5 fragments of MfERF026: full length (a), N-terminal+ERF domain (b), ERF domain (c), ERF domain+C-terminal (d), and C-terminal (e). The details of the 5 fragments are shown in FIG. 6A.

The PCR system is shown in Table 7.

TABLE 7

| PCR system | |
|---|---|
| Reagent | Consumption (μL) |
| pEASY ®-Blunt-MfERF026 plasmid (100 ng/μL) | 2 |
| 5xPrime STAR GXL Buffer | 10 |
| Prime STAR GXL DNA Ploymerase | 1 |

TABLE 7-continued

| PCR system | |
| --- | --- |
| Reagent | Consumption (μL) |
| dNTP Mixture(2.5 mmol/L) | 4 |
| PF(5 μmol/L) | 3 |
| PF(5 μmol/L) | 3 |
| RNase free ddH$_2$O | Supplementing to 50.0 μL |

PCR conditions included: initial denaturation at 98° C. for 5 min; denaturation at 98° C. for 30 s; annealing at 60° C. for 30 s; extension at 68° C. for 1 min and 30 s, 30 cycles; post-extension at 68° C. for 10 min; and storage at 16° C. for 10 min.

The 5 fragments of MfERF026: full length (a), N-terminal+ERF domain (b), ERF domain (c), ERF domain+C-terminal (d), and C-terminal (e) were inserted into a pGBKT7 vector separately to construct a fusion expression vector.

Construction of Fusion Expression Vector (1) After the PCR was completed, a target fragment was recovered using a SanPrep column DNA gel recovery kit of Sangon Biotech Co., Ltd., which was performed according to the instructions of the kit.

(2) A pBE empty plasmid was double-digested with BamHI and Nod using an enzyme digestion system shown in Table 8.

TABLE 8

| Enzyme digestion system | |
| --- | --- |
| Reagent | Consumption (μL) |
| pGBKT7 plasmid (100 ng/μL) | 10 |
| 10xKbuffer | 1 |
| BamHI(15 U/μL) | 1 |
| NotI(10 U/μL) | 1 |
| ddH$_2$O | Supplementing to 20 μL |

The enzyme digestion system was mixed for digestion at 37° C. for 1 h. After the PCR was completed, a linearized plasmid vector was recovered using a SanPrep column DNA gel recovery kit of Sangon Biotech Co., Ltd., which was performed according to the instructions of the kit.

(3) According to a molar ratio of the target fragment to the vector at (3-10):1, the target gene fragment was ligated to the pGBKT7 linearized vector, transformed into *E. coli* competent cells DH5α, spread onto a plate, and positive clones were selected to allow PCR detection. The obtained positive clones verified by sequencing were subjected to expanded culture, and a plasmid was extracted for later use.

5 obtained fusion expression vectors were transferred into AH109 yeast separately, and yeast transformants of the 5 fusion expression vectors were separately cultured in an SD/-Trp medium (i.e., yeast-deficient medium, SD medium lacked tryptophan) and an X-α-gal-added SD/-Trp/-His/-Ade medium (i.e., the SD medium lacked tryptophan, histidine, and adenine).

Figure 6B:
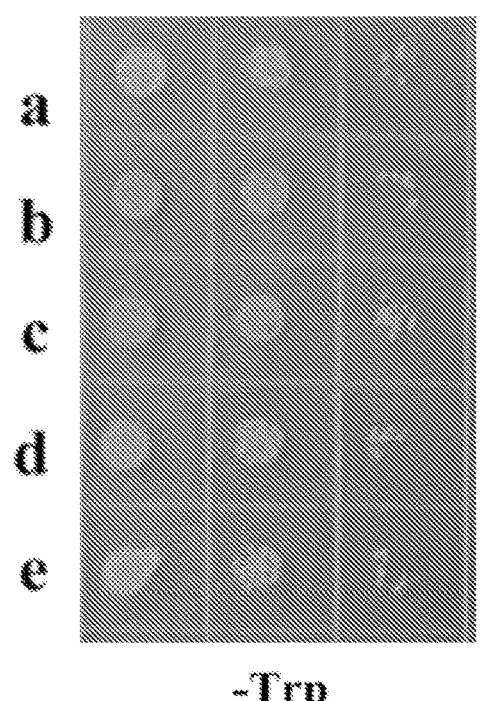

The culture results of the yeast transformants of the 5 fusion expression vectors on different media are shown in FIG. 6B.

Figure 6B:
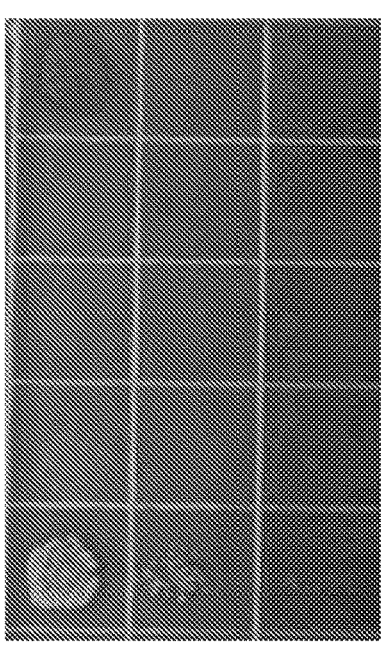

As shown in FIG. 6, the 5 yeast transformants of fusion expression vectors grew well on SD/-Trp medium. On the SD/-Trp/-His/-Ade medium supplemented with X-α-gal, only blue yeast colonies were observed in a and e. This indicated that the β-galactosidase reporter gene had been transcriptionally activated and exhibited a desirable activity. The results proved that the MfERF026 protein had a transcription activation activity, and its transcription activation domain was located at the C-terminal.

Example 5

Obtaining Transgenic *M. sativa* with Inhibited Expression of MfERF026

1. Construction of Inhibition Expression Vector pCAM1307-RNAi-MfERF026

The *M. falcata* cDNA was obtained using the method in Example 1.

Figure 7A:
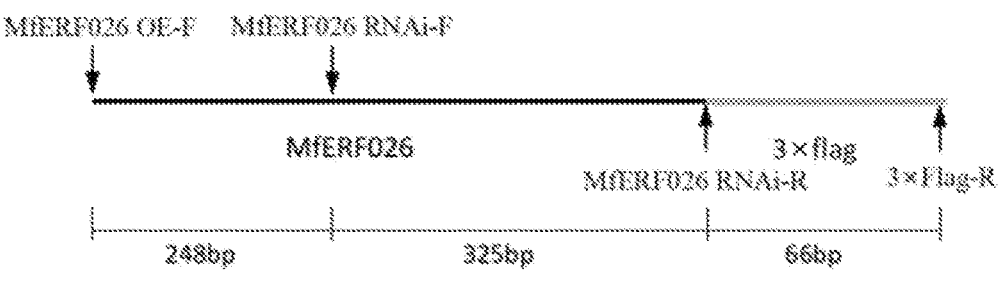
FIGS. 7A-7G show the verification results of a MfERF026 transgenic line.

PCR was conducted using MfERF026 RNAi-F and MfERF026 RNAi-R (the primer amplification fragments are shown in FIG. 7A), to obtain a full-length cDNA of RNAi-MfERF026 with BamHI and XbaI restriction sites. The PCR system and PCR conditions were the same as those in Example 3. The information of primer pair including MfERF026 RNAi-F and MfERF026 RNAi-R is shown in Table 9, and the amplified target fragment is set forth in SEQ ID NO: 17.

TABLE 9

| Sequence information of primers MfERF026 RNAi-F and MfERF026 RNAi-R | | |
| --- | --- | --- |
| Primer name | Primer ID | 5'-3' |
| MfERF026 RNAi-F | SEQ ID NO: 14 | CGGGATCCTTCAGAGGTGAAGACACACGTAGATGTAGCTGCT CTTAGTAT |
| MfERF026 RNAi-R | SEQ ID NO: 15 | GCTCTAGACTAGCTATAGTTATTATAAATG |

After the PCR was completed, the agarose gel electrophoresis was conducted to detect the PCR products, and a target fragment was obtained by determining the size of the band.

After the PCR was completed, a target fragment (about 330 bp) was recovered using a SanPrep column DNA gel recovery kit of Sangon Biotech Co., Ltd., and the operations were done according to the instructions of the kit.

An empty plasmid pCAM1307 (hereinafter referred to as p1307) was digested with BamHI and XbaI, and the enzyme digestion system is shown in Table 10.

17

TABLE 10

Enzyme digestion system

| Reagent | Consumption (μL) |
| --- | --- |
| p1307 plasmid (100 ng/μL) | 10 |
| 10xK Buffer | 1 |
| BamH I | 1 |
| XbaI | 1 |
| ddH$_2$O | Supplementing to 20 μL |

The enzyme digestion system was mixed for digestion at 37° C. for 1 h. After the PCR was completed, a linearized plasmid vector was recovered using a SanPrep column DNA gel recovery kit of Sangon Biotech Co., Ltd., and the operations were done according to the instructions of the kit.

According to a molar ratio of the target fragment to the vector at (3-10):1, the target gene fragment was ligated to the p1307 linearized vector, transformed into *E. coli* competent cells DH5α, spread onto a plate, and positive clones were selected to allow PCR detection. The obtained positive clones verified by sequencing were subjected to expanded culture, and a plasmid was extracted for later use.

2. Transformation of *Agrobacterium* EHA105 with the Inhibition Expression Vector pCAM1307-RNAi-MfERF026

5 μL of the inhibition expression vector pCAM1307-RNAi-MfERF026 at a concentration of 100 ng/μL was pipetted and added to 50 μL of EHA105 competent cells. After snap-freezen in liquid nitrogen for 2 min and heat shocked at 42° C. for 30 s, the cells were added into 600 μL of a YEB liquid medium and cultured at 28° C. and 190 rpm for 4 h.

After the culture was completed, 80 μL of a resulting bacterial solution was spread on a YEB solid medium containing kanamycin (50 mg/L) and rifampicin (75 mg/L), and cultured upside down at 28° C. for 2 d.

After the culture was completed, positive colonies are selected. The selected positive single colonies were subjected to expanded culture until the OD$_{600}$ value was 0.6 to 0.8, an obtained *Agrobacterium* bacteria solution was centrifuged at 2,400 rpm at room temperature for 15 min, a supernatant was discarded, and the cells were suspended until the OD$_{600}$ value reached 0.2 to 0.3 to prepare an infection solution for later use.

3. *Agrobacterium* EHA105-Mediated Leaf Disk Transformation of *M. sativa*

The *M. sativa* "Zhongmu No. 1" was selected as a plant material, and the *M. sativa* leaves in desirable growth condition for four to six weeks were selected as an infection material.

The *M. sativa* was transformed by an EHA105-mediated leaf disc method:

After the infection material was washed with ultrapure water, an appropriate amount of a mixed solution including hypochloric acid rinsing solution and Tween-20 was added (the Tween-20 and hypochloric acid rinsing solution in the mixed solution were at a volume ratio of 1:3000; the hypochloric acid in the hypochloric acid rinsing solution had a mass percentage of 7%; and the hypochloric acid rinsing solution was purchased from Taobao (sterilization 99.99%, imported Clorox, 1 L*2 bottle, household indoor clothing disinfection, hypochloric acid disinfection bleach), such that the mixed solution covered the leaves to allow sterilization for 10 min to 13 min.

The infection solution prepared in step 2 was mixed with the sterilized trifoliate plant, the leaves were infiltrated at 0.08 MPa to 0.09 MPa under vacuum for 10 min, ultrasonicated (40 kHz) at room temperature for 4 min to 5 min, and infiltrated again at 0.08 MPa to 0.09 MPa under vacuum 10 min.

After the vacuum infiltration was completed, the *Agrobacterium* suspension was discarded, the *Agrobacterium* on the leaf surface was removed by absorbing with sterilized filter paper, the treated trifoliate plant was spread on the co-culture medium, and cultured in the dark for 24 h to 30 h. The obtained explants were transplanted into a selective medium to allow callus induction culture, where subculture was conducted every 2 weeks for 5 to 6 weeks.

The calli in desirable growth conditions were transferred to an MSBK medium and cultured for 10 d to 14 d until green embryoid appeared.

The calli with green embryoid were transferred into an SH9 medium to allow shoot differentiation. Subculture was conducted every 3 to 4 weeks until the shoots grew up, which generally took 6 to 8 weeks on this medium. When the shoots grew 2 to 3 fully expanded trifoliate leaves, the shoots were transferred into an MSO medium for rooting culture to obtain rooted plants (if the strong-growing seedlings were difficult to take root within a month, 1 mg/L IAA was added).

The rooted plants were planted into a matrix including vermiculite and perlite at a volume ratio of 1:1 to allow acclimatization. Surviving plants were transferred to a medium with nutrient soil and vermiculite at a volume ratio of 1:1 for culture.

4. Detection of transgenic *M. sativa*

The transgenic lines were verified using PCR and Q-PCR.

In this step, wild-type *M. sativa* plants were used as controls, where control experimental material was the leaf tissues of wild-type *M. sativa* "Zhongmu No. 1" grown normally for 30 d, and their treatment and detection methods were the same as those of the transgenic plants.

DNA from leaves of transgenic plants and leaves of wild plants that had survived for 30 d were obtained using the CTAB method to allow PCR identification.

The PCR was conducted using MfERF026 RNAi-F and 3xFlag-R primers (the primer amplification fragment is shown in FIG. 7A). The information of primers MfERF026 RNAi-F and 3xFlag-R is shown in Table 11.

TABLE 11

Primer information

| Primer name | Primer ID | 5'-3' |
| --- | --- | --- |
| MfERF026 RNAi-F | SEQ ID NO: 14 | CGGGATCCTTCAGAGGTGAAGACACACGTAGATGTAGCTGCTC TTAGTAT |
| 3xFlag-R | SEQ ID NO: 16 | CTACTTATCGTCATCGTCCTTGTA |

The PCR system is shown in Table 12.

TABLE 12

| PCR system | |
| --- | --- |
| Reagent name | Consumption (µL) |
| 10x Buffer | 2.5 |
| dNTPs (2.5 mM each) | 2.0 |
| MfERF026 RNAi-F | 3.0 |
| 3xflag-PR | 3.0 |
| DNA | 2 |
| rTaqDNA Polymerase(5 U/µL) | 0.125 |
| ddH$_2$O | Supplementing to 25 µL |

PCR conditions included: initial denaturation at 98° C. for 5 min; denaturation at 98° C. for 10 s; annealing at 57° C. for 30 s; extension at 68° C. for 1 min, 30 cycles; post-extension at 68° C. for 10 min; and storage at 4° C.

After the PCR was completed and the PCR product was obtained, agarose gel electrophoresis was conducted to detect whether a target band was produced and a size of the target band, so as to determine the positive strain.

Figure 7B:
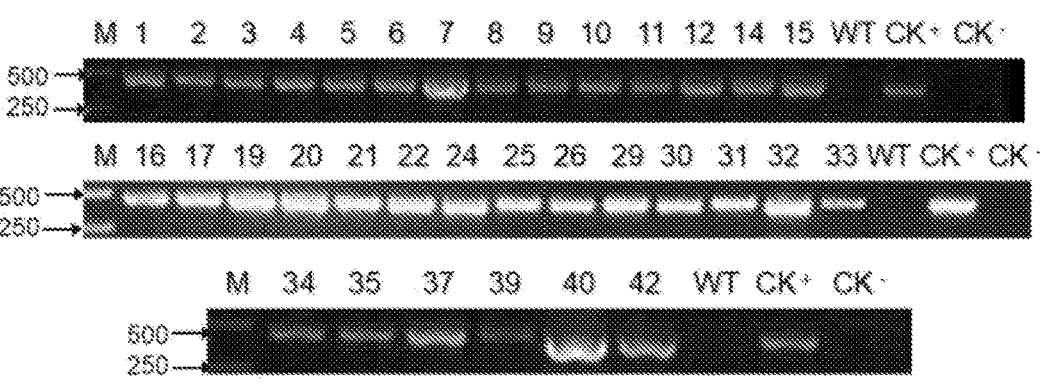
Figure 7C:
Figure 7C:
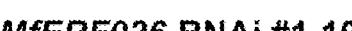
Figure 7C:
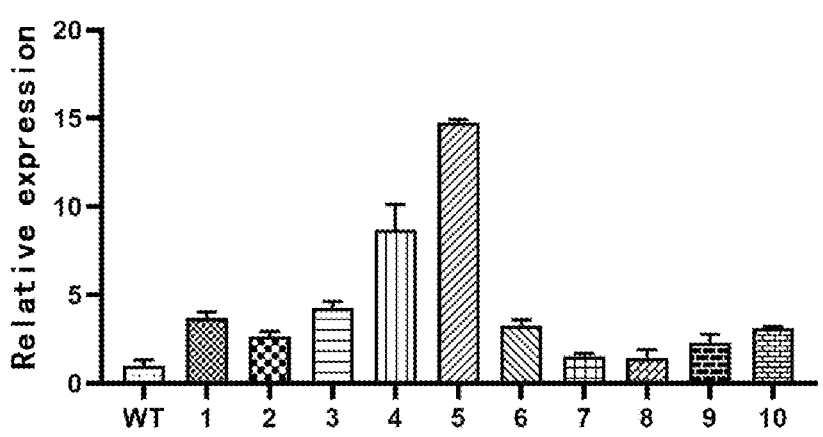
Figure 7D:
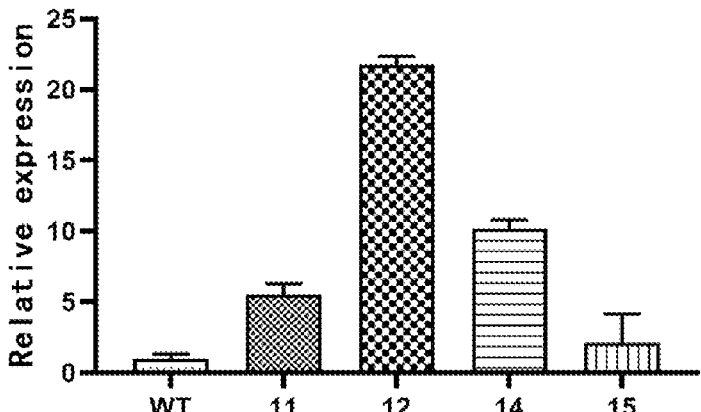
Figure 7E:
Figure 7E:
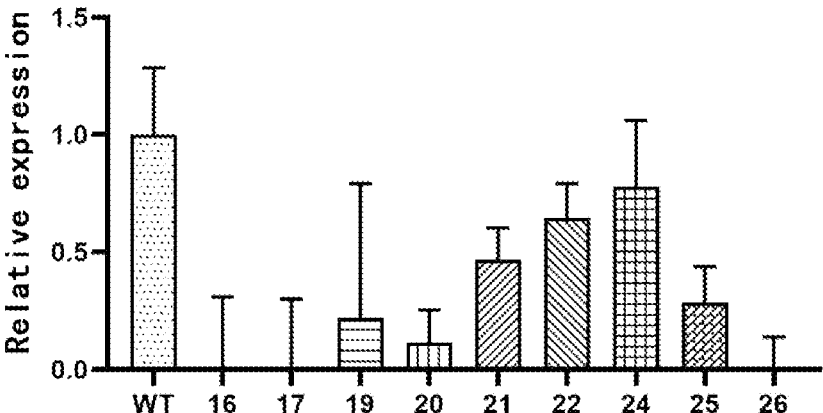
Figure 7F:
Figure 7F:
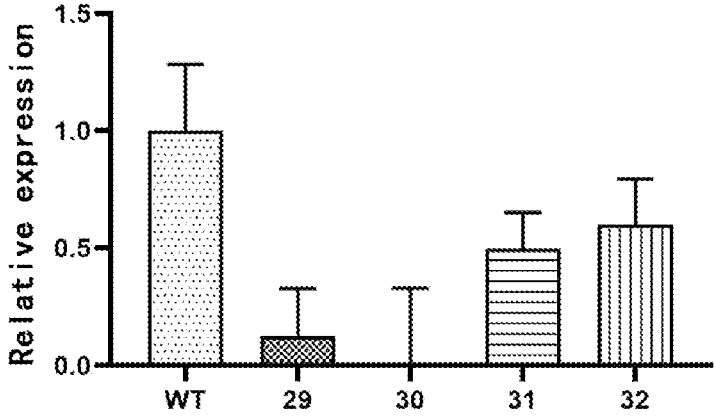
Figure 7G:
Figure 7G:
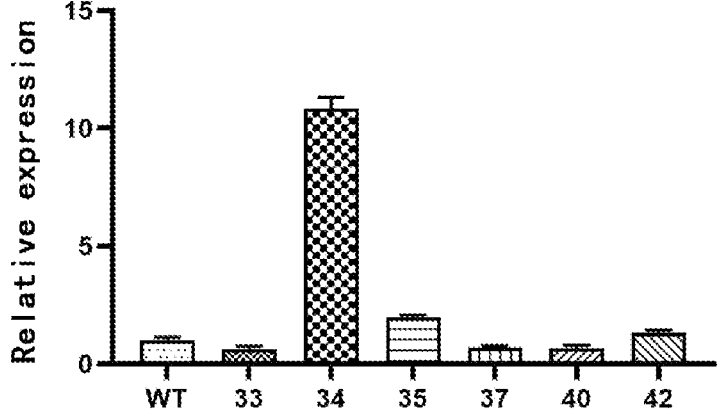

The gel electrophoresis pattern of the PCR product is shown in FIG. 7B.

RNA was extracted from the leaves of the lines that were initially detected as positive and reverse transcribed into cDNA, and then fluorescence quantitative RT-qPCR was conducted to calculate the relative expression level of MfERF026 in each line. Wild-type *M. sativa* RNA at the same growth period was extracted and reverse transcribed into cDNA, and quantitative RT-qPCR was conducted to calculate the relative expression level of MfERF026 as a control group.

RT-qPCR was conducted using the MfERF026 DL-F and MfERF026 DL-R as primers according to the instructions of a Reverse Transcription Kit (#RR047Q, TAKARA Biotechnology). The information of primers MfERF026 DL-F and MfERF026 DL-R is shown in Table 2.

The relative expression level of MfERF026 was calculated based on the RT-qPCR results, and the calculation method and reference gene were the same as those in Example 2.

The RT-qPCR detection results of MfERF026 in transgenic *M. sativa* and wild-type *M. sativa* are shown in Table 13 and FIGS. 7C-7G.

TABLE 13

| RT-qPCR detection results of MfERF026 in transgenic *M. sativa* and wild-type *M. sativa* | | | | | | |
| --- | --- | --- | --- | --- | --- | --- |
| Root system ID | WT | 1 | 2 | 3 | 4 | 5 |
| Relative expression level | 1 | 3.696395702 | 2.666397516 | 4.272497773 | 8.705489094 | 14.75885607 |
| Root system ID | WT | 6 | 7 | 8 | 9 | 10 |
| Relative expression level | 1 | 3.272519645 | 1.548315837 | 1.435649964 | 2.310759365 | 3.128273539 |
| Root system ID | WT | 11 | 12 | 14 | 15 | |
| Relative expression level | 1 | 5.539331733 | 21.79154398 | 10.15253741 | 2.137380309 | |
| Root system ID | WT | 16 | 17 | 19 | 20 | 21 |
| Relative expression level | 1 | 0.000170468 | 0.000722038 | 0.219165015 | 0.114911495 | 0.466560473 |
| Root system ID | WT | 22 | 24 | 25 | 26 | |
| Relative expression level | 1 | 0.645638668 | 0.776569093 | 0.284394388 | 0.000189571 | |
| Plant line ID | WT | 29 | 30 | 31 | 32 | |
| Relative expression level | 1 | 0.125675276 | 0.00035771 | 0.498250989 | 0.600333031 | |
| Root system ID | WT | 33 | 34 | 35 | 37 | 40 | 42 |
| Relative expression level | 1 | 0.635141522 | 10.83997828 | 1.969879598 | 0.700018392 | 0.662697461 | 1.319191848 |

Note:
WT refers to wild-type

According to the quantitative results shown in Table 13 and FIG. 7C-7G, MfERF026 expression of the transgenic lines was significantly reduced compared with that of the wild-type (WT). The results proved that MfERF026 was transferred into the *M. sativa* genome and showed inhibited expression. Transgenic lines #16, #17, #26, and #29 showed the best inhibitory effects, so the lines #16, #17, #26, and #29 were selected for subsequent experiments.

6. Developmental Phenotypes, Drought Tolerance Experiments, and Cold Tolerance Experiments of Transgenic Lines with Inhibited Expression (1) Cuttings of Transgenic *M. sativa*

On the basis of Experiment 5, the stems and leaves of transgenic lines #16, #17, #26, and #29 with desirable growth status were selected, their branches about 7 cm long were cut off at an angle, and a bottom incision of each branch was dipped into a rooting powder (Solarbio, Cat. No. R8240) solution (1 g/L) for 10 min, inserted into the thoroughly poured vermiculite, leaving only the nodes on the surface. White and strong roots grew in about 2 weeks, and were transplanted into a matrix with vermiculite and nutrient soil at a ratio of 3:2 (v/v), while the wild-type *M. sativa* from the same batch were also cut as a control group. The number of test samples in each group was >30.

(2) Developmental Phenotypes of Transgenic Lines with Inhibited Expression

Wild-type plants and transgenic plants grown for 30 d in a medium with vermiculite and nutrient soil at a ratio of 3:2 (v/v) were selected for measurement, statistics, and analysis of the developmental phenotypes.

Figure 8:
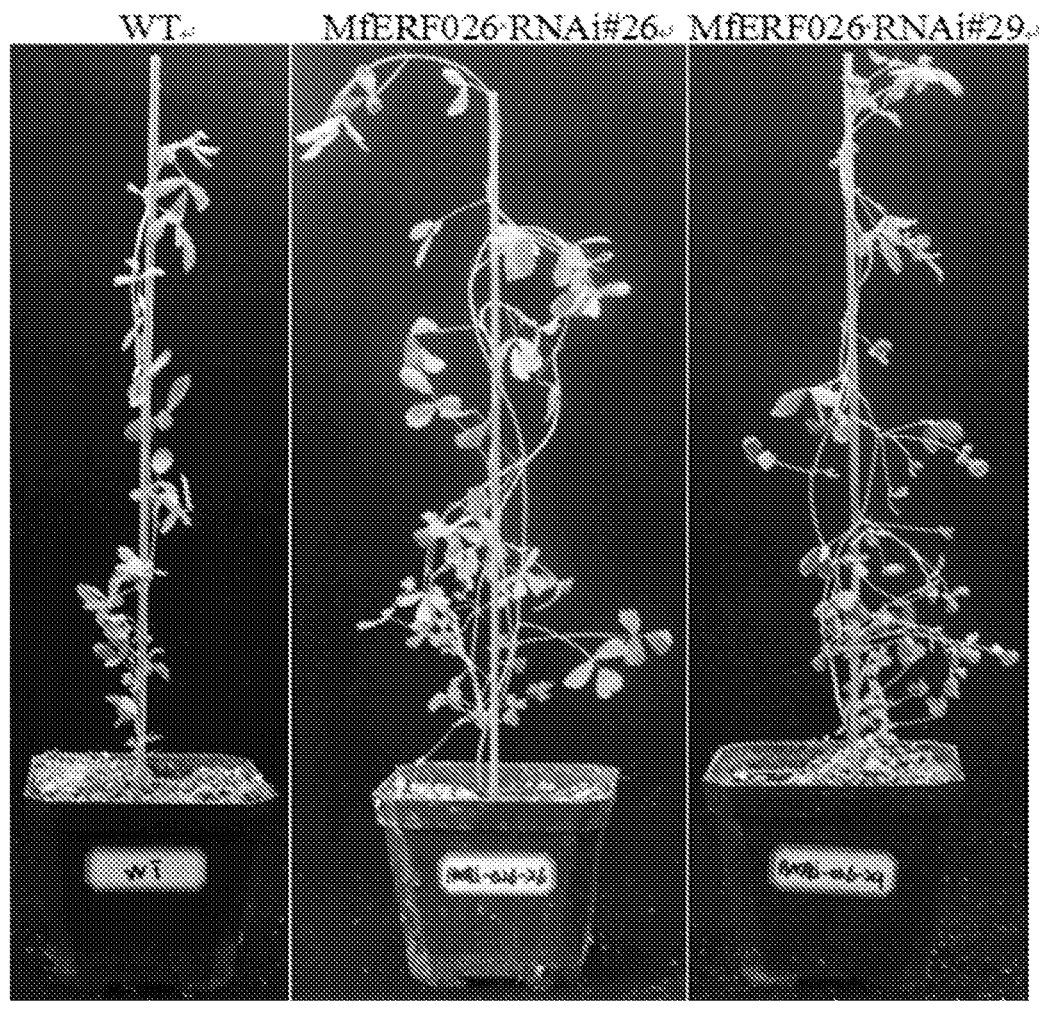
FIG. 8 shows the growth of transgenic lines #26 and #29 and wild-type *M. sativa;*
Figure 9A:
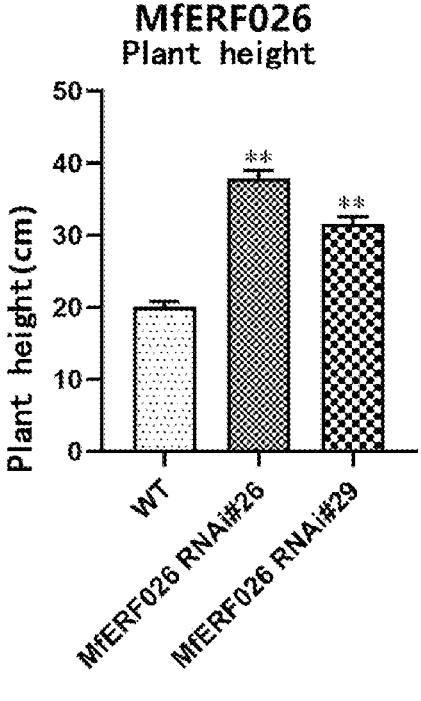
FIGS. 9A-9D show the statistical results of plant height, number of tillers, number of trifoliate leaves, and number of segments of wild-type plants and transgenic plants #26 and #29.
Figure 9B:
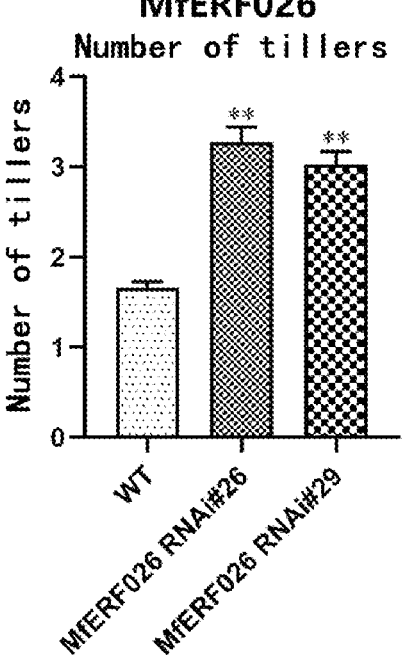
Figure 9C:
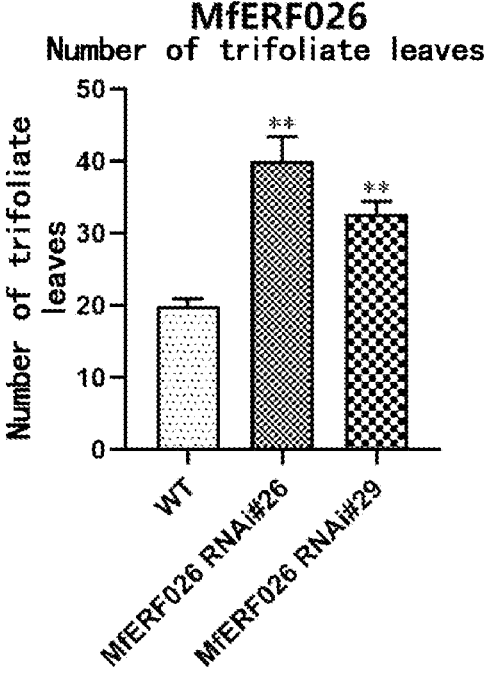
Figure 9D:
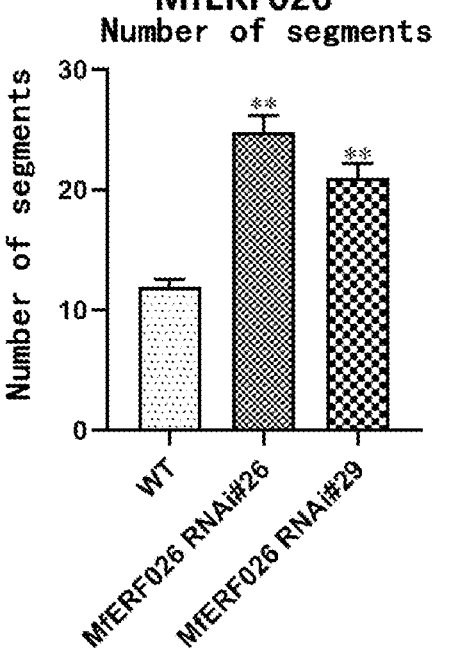
Figure 10A:
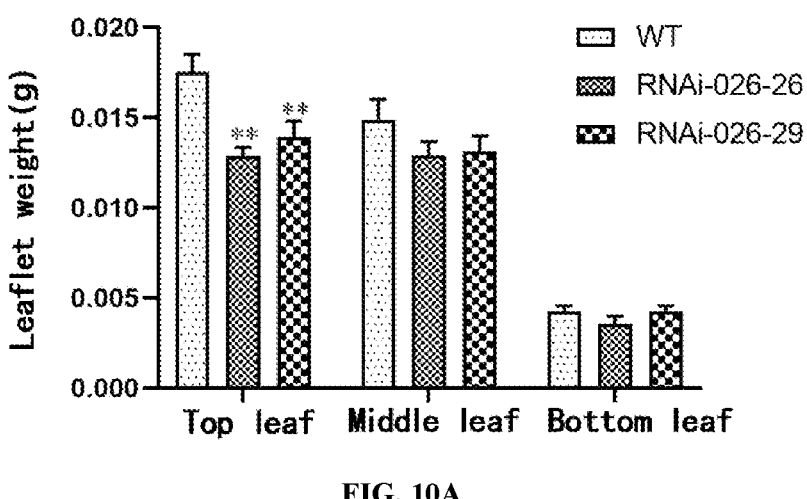
FIGS. 10A-10C show the statistical results of leaflet weight, leaflet area, and leaflet specific leaf weight of wild-type plants and transgenic plants #26 and #29.
Figure 10B:
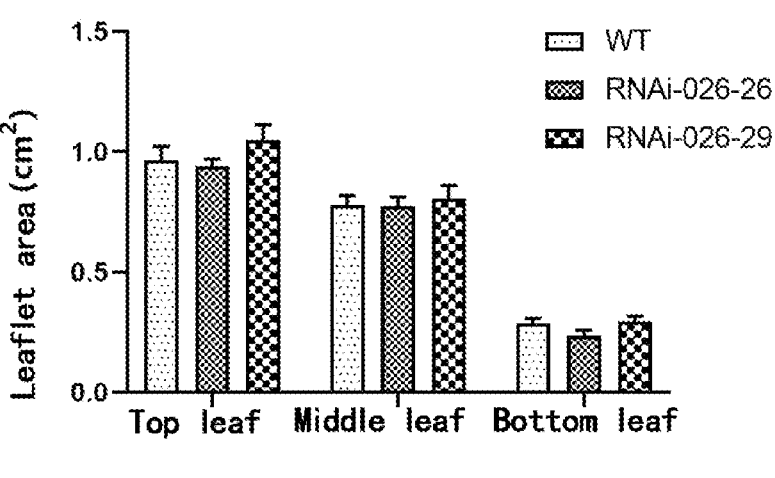
Figure 10C:
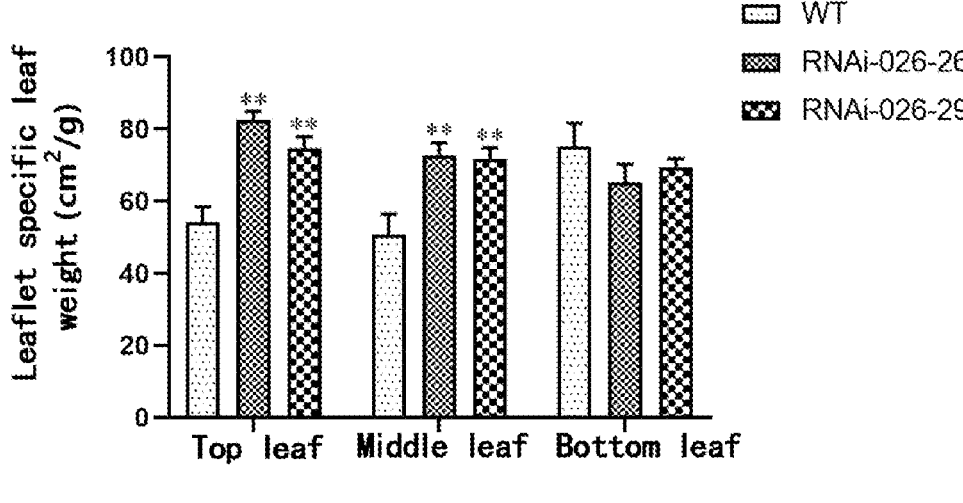
Figure 11A:
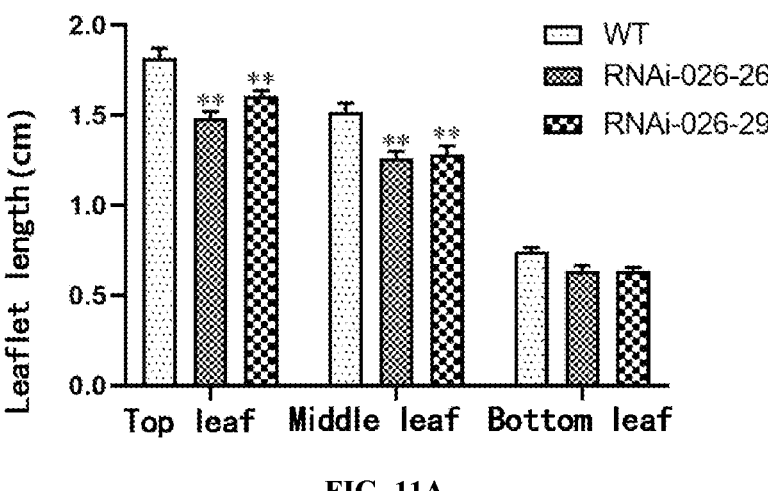
FIGS. 11A-11C show the statistical results of leaflet length, leaflet width, and leaflet aspect ratio of wild-type plants and transgenic plants #26 and #29.
Figure 11B:
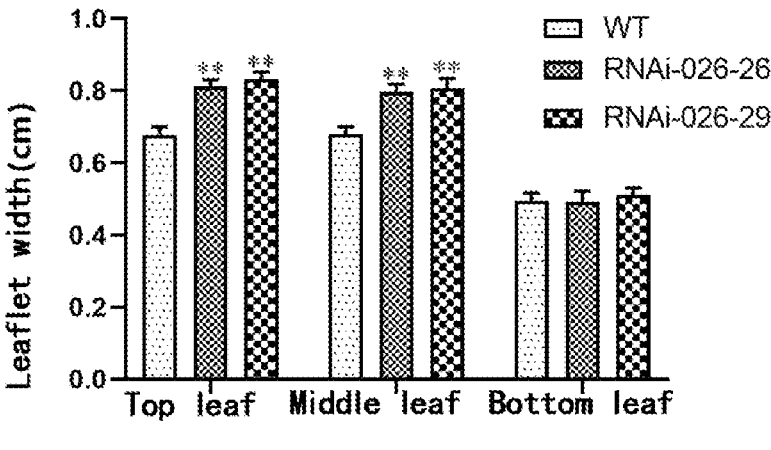
Figure 11C:
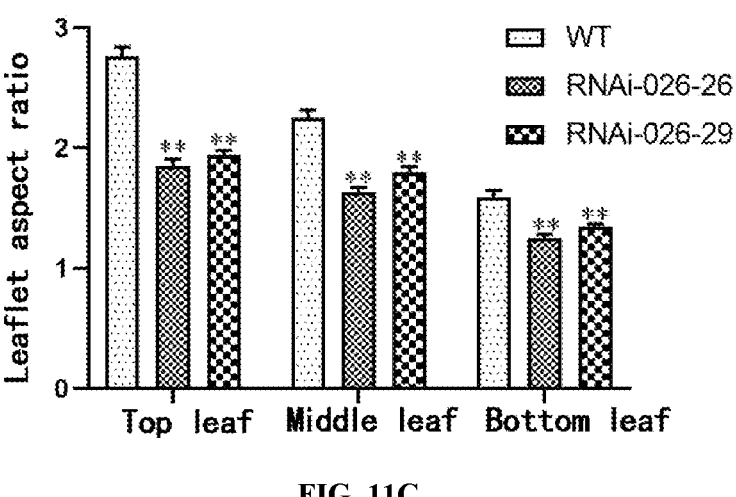

FIG. 8 showed the growth of transgenic lines #26 and #29 and wild-type *M. sativa*.

The statistical results of developmental phenotypes of wild-type plants and transgenic plants are shown in Tables 14 to 15 and FIG. 9 to FIG. 11C. The plant height, number of tillers, number of trifoliate leaves, and number of segments of wild-type plants and transgenic plants are shown in Table 14 and FIGS. 9A-9D. The statistical results of leaflet weight, leaflet area, and leaflet specific leaf weight (i.e., the ratio of leaflet weight to leaflet area) of wild-type plants and transgenic plants are shown in Table 15 and FIGS. A-C. The leaflet length, leaflet width, and leaflet aspect ratio of wild-type plants and transgenic plants are shown in Table 15 and FIGS. 11A-11C.

TABLE 14

Plant height, number of tillers, number of trifoliate leaves, and number of segments of wild-type plants and transgenic plants

| Group | Number of segments | Number of tillers | Plant height | Number of trifoliate leaves |
|---|---|---|---|---|
| WI | 11.96 | 1.663 | 20.05 | 19.94 |
| MfERF026 RNAi#26 | 24.79 | 3.274 | 37.84 | 40.04 |
| MfERF026 RNAi#29 | 21.02 | 3.025 | 31.59 | 32.63 |

TABLE 15

Statistical results of leaflet of wild-type plants and transgenic plants

| Group | Leaf type | Leaf weight | Leaf area | Specific leaf weight | Leaf length | Leaf width | Leaf aspect ratio |
|---|---|---|---|---|---|---|---|
| WT | Top leaf | 0.01754 | 0.9659 | 54.16 | 1.818 | 0.6783 | 2.762 |
| | Middle leaf | 0.01489 | 0.7766 | 50.7 | 1.518 | 0.6806 | 2.251 |
| | Bottom leaf | 0.004273 | 0.288 | 75.18 | 0.7441 | 0.4953 | 1.59 |
| MfERF026 RNAi#26 | Top leaf | 0.01286 | 0.9396 | 82.58 | 1.486 | 0.8125 | 1.851 |
| | Middle leaf | 0.01291 | 0.7751 | 72.83 | 1.261 | 0.7974 | 1.631 |
| | Bottom leaf | 0.00356 | 0.2338 | 65.17 | 0.6358 | 0.4916 | 1.25 |
| MfERF026 RNAi#29 | Top leaf | 0.01395 | 1.049 | 74.77 | 1.607 | 0.8319 | 1.942 |
| | Middle leaf | 0.01312 | 0.806 | 71.72 | 1.285 | 0.8073 | 1.795 |
| | Bottom leaf | 0.004273 | 0.2943 | 69.45 | 0.6362 | 0.5111 | 1.344 |

As shown in Tables 14 and 15 and FIG. 8 to FIG. 11C, compared with the control (WT) plants, the plants with inhibited expression had increased plant height, increased number of tillers, and increased number of segments and number of trifoliate leaves. Compared with the control (WT) plants, the plants with inhibited expression had reduced top leaf weight, reduced leaflet length but increased leaflet width, no significant difference in leaf area, increased leaflet specific leaf weight, and decreased aspect ratio.

(3) Drought Tolerance Experiment of Transgenic Lines with Inhibited Expression

The wild-type plants and transgenic lines #16, #17, #26, and #29 that were grown for 30 d in a soil matrix with vermiculite and nutrient soil a volume ratio of 3:2 were saturated and the drought tolerance experiment was started, where watering was stopped for 3 weeks and resumed for 1 week. After the rewatering was completed, the survival rate of the *M. sativa* in the experimental group and the control group was calculated, and the changes in electrical conductivity and physiological and biochemical indicators of the *M. sativa* in the experimental group and the control group before and after the experiment were detected and compared. #16 had 20 test plants; #17, #26, and #29 had 21 test plants separately; wild-type (WT) had 26 test plants.

Method for measuring conductivity: i. the leaves to be measured were placed in a 50 mL centrifuge tube containing 25 mL of ultrapure water; ii. the centrifuge tube was placed into a vacuum pump, vacuumized (<0.09 MPa) for 15 min, and then transferred into a shaker, and balanced by shaking at 230 rpm at room temperature for 1 h; iii. the conductivity meter was used to measure the electric conductivity of the liquid in the centrifuge tube, and an initial value S1 was recorded; iv. the centrifuge tube containing the sample was treated in a boiling water bath tank for 15 min, and then transferred into a shaker, balanced by shaking at 230 rpm at room temperature for 1 h, and the liquid in the tube was cooled naturally to room temperature; v. the electric conductivity of the liquid in the centrifuge tube was measured and the value was recorded as S2; vi. the electric conductivity of ultrapure water was measured at the same time, and the value was recorded as S0; vii. a relative electric conductivity of the sample leaves was measured based on S1 and S2 of each sample and the electric conductivity S0 of ultrapure water. The calculation formula of electric conductivity was: relative electric conductivity=(S1-S0)/(S2-S0).

Figure 12:
FIG. 12 shows the growth status of wild-type plants and transgenic plants before the drought tolerance test.
Figure 13:
FIG. 13 shows the growth status of wild-type plants and transgenic plants under drought stress for 3 weeks.
Figure 14:
FIG. 14 shows the growth status of wild-type plants and transgenic plants after rewatering for one week.
Figure 15:
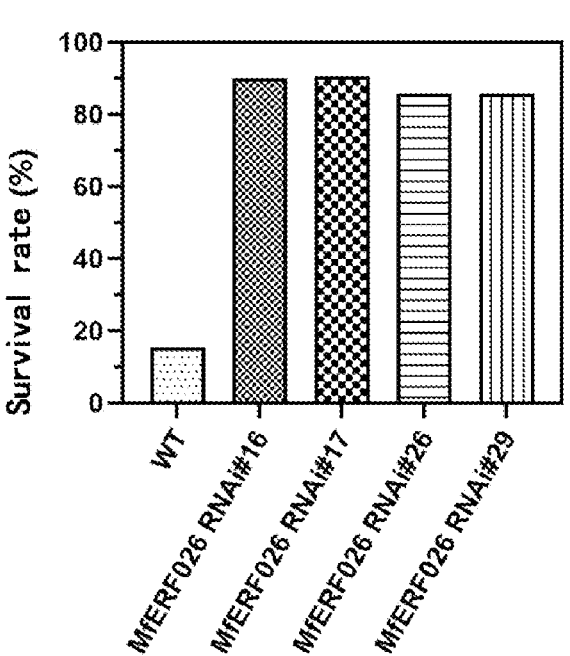
FIG. 15 shows the statistical results of survival rates of the drought tolerance test.
Figure 16:
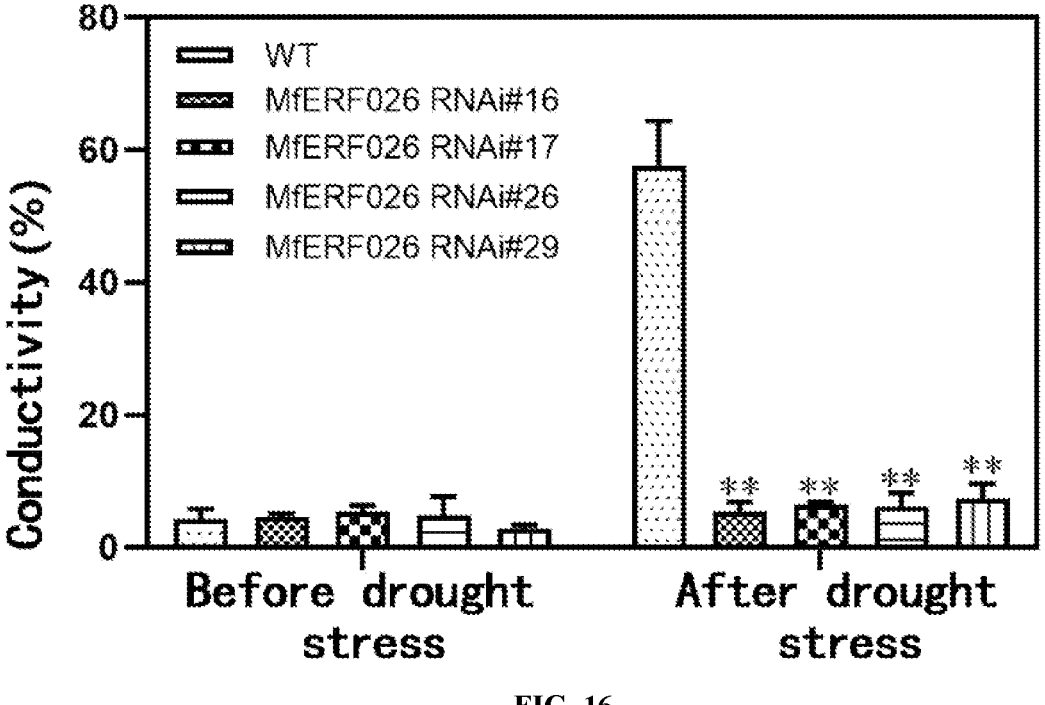
FIG. 16 shows the statistical results of the electrical conductivity before and after drought stress.
Figure 17A:
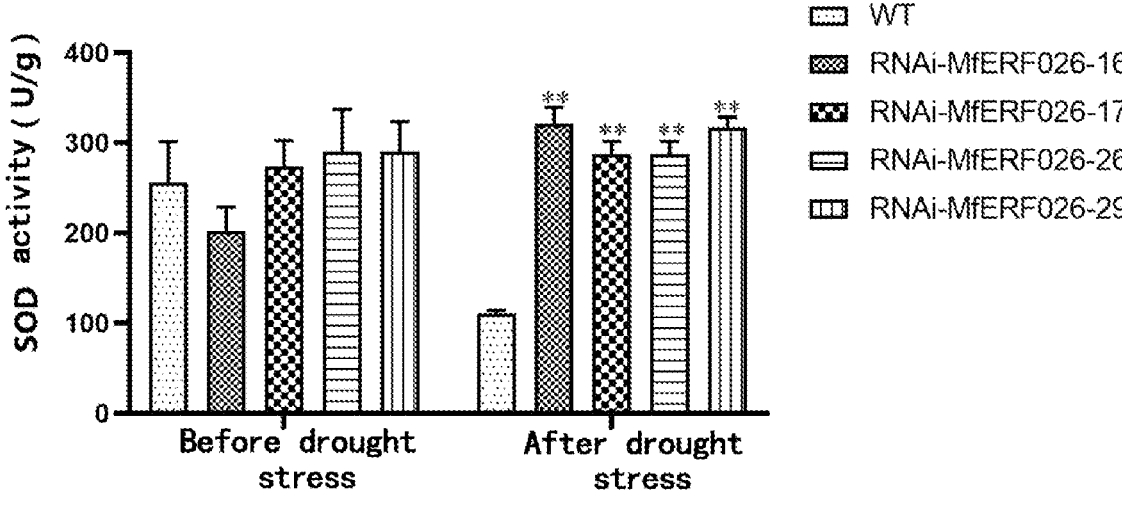
FIGS. 17A-17F show the measurement results of physiological and biochemical indicators of drought stress for MfERF026.
Figure 17B:
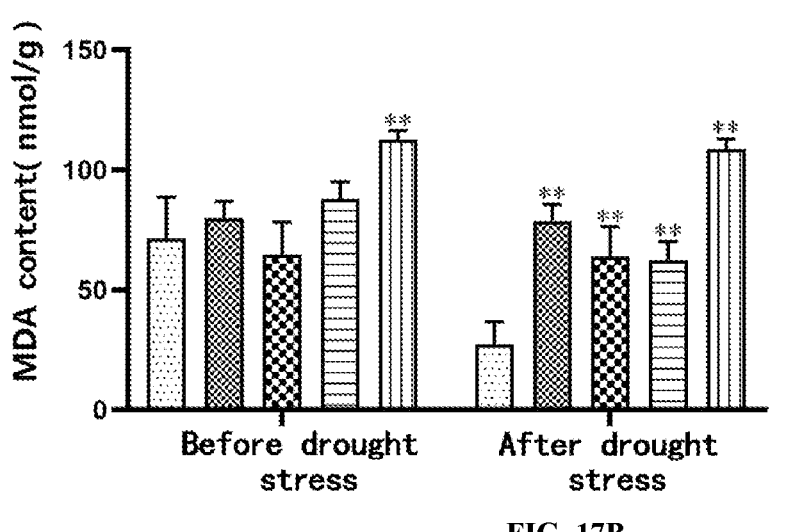
Figure 17C:
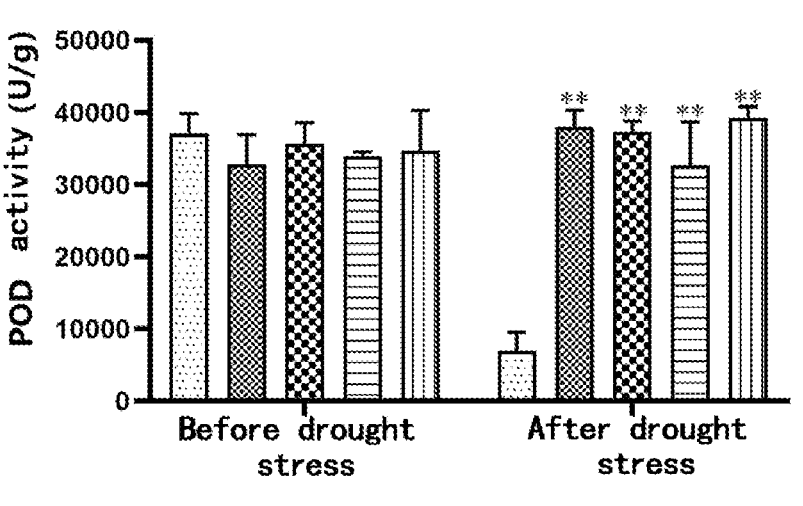
Figure 17D:
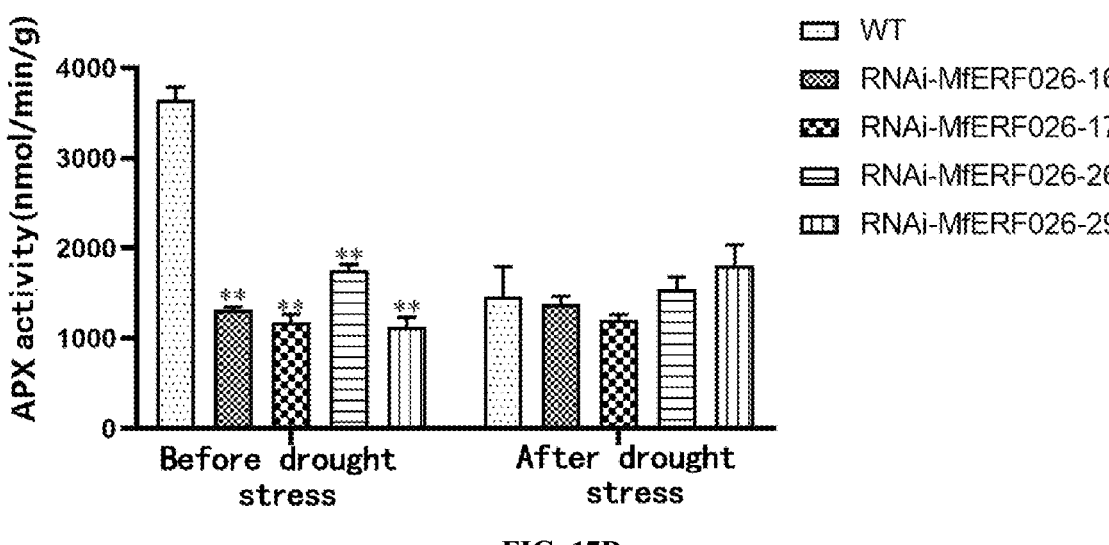
Figure 17E:
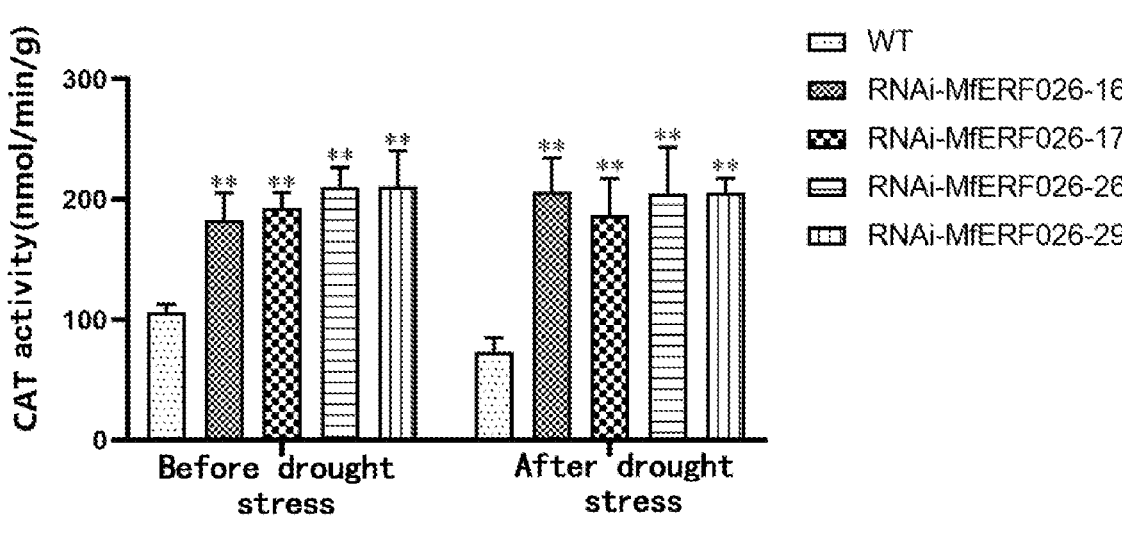
Figure 17F:
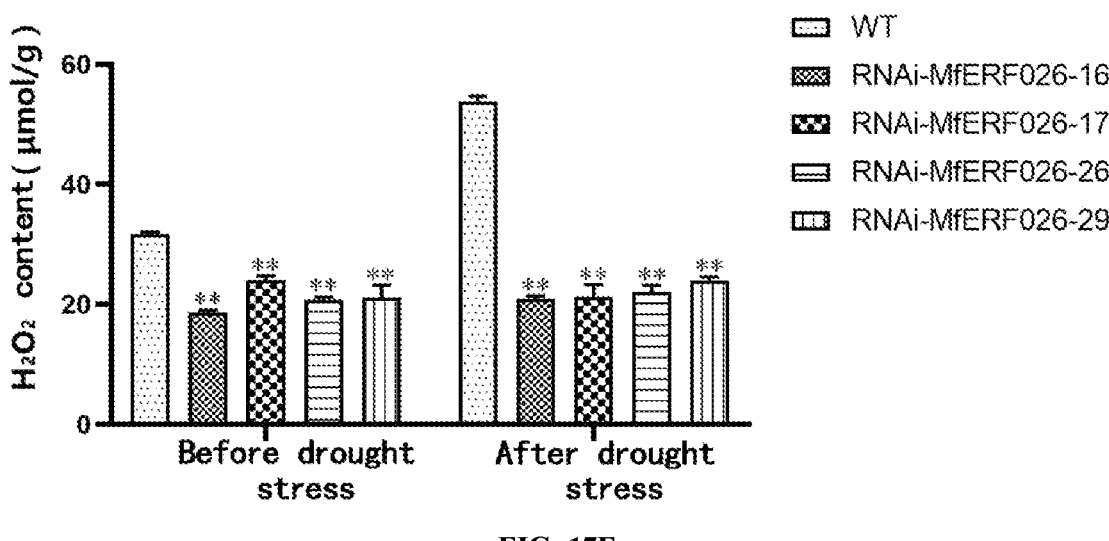

The drought tolerance test results of wild-type plants and transgenic lines are shown in Tables 16 and 17 and FIG. 12 to FIG. 16. FIG. 12 showed the growth status of wild-type plants and transgenic plants before the drought tolerance test; FIG. 13 shows the growth status of wild-type plants and transgenic plants under drought stress for 3 weeks; FIG. 14 shows the growth status of wild-type plants and transgenic plants after one week of rewatering. FIG. 12 to FIG. 14 show the wild-type plants, transgenic plant #16, transgenic plant #17, transgenic plant #26, and transgenic plant #29 from left to right in sequence. The statistical results of survival rate after drought stress are shown in Table 16 and FIG. 15; the statistical results of electrical conductivity before and after drought stress are shown in Table 17 and FIG. 16.

TABLE 16

Statistical results of drought tolerance survival rates of wild-type plants and transgenic lines

| Group | Survival rate |
|---|---|
| WT | 15.38% |
| MfERF026 RNAi#16 | 90% |
| MfERF026 RNAi#17 | 90.48% |
| MfERF026 RNAi#26 | 85.71% |
| MfERF026 RNAi#29 | 85.71% |

TABLE 17

Statistical results of drought tolerance electric conductivity of wild-type plants and transgenic lines

| Group | Electric conductivity Before stress | After stress |
|---|---|---|
| WT | 4.35 | 57.68 |
| MfERF026 RNAi#16 | 4.618 | 5.402 |
| MfERF026 RNAi#17 | 5.4 | 6.42 |
| MfERF026 RNAi#26 | 4.928 | 6.204 |
| MfERF026 RNAi#29 | 2.86 | 7.388 |

As shown in Tables 16 and 17 and FIG. 12 to FIG. 16, compared with wild-type WT, the MfERF026 transgenic line with inhibited expression had higher survival rate, better cell membrane permeability, lower damage, and obviously stronger drought tolerance.

Before and after the experiment, the physiological and biochemical indicators of *M. sativa* in the experimental group and the control group were detected using kits from Suzhou Comin Biotechnology Co., Ltd.

The measurement results of physiological and biochemical indicators of wild-type *M. sativa* and transgenic *M. sativa* under drought stress are shown in Table 18 and FIGS. 17A-17F.

TABLE 18

Measurement results of physiological and biochemical indicators of wild-type *M. sativa* and transgenic *M. sativa* under drought stress

| Group | APX Before | APX After | CAT Before | CAT After | H$_2$O$_2$ Before | H$_2$O$_2$ After | MDA Before | MDA After | POD Before | POD After | SOD Before | SOD After |
|---|---|---|---|---|---|---|---|---|---|---|---|---|
| WT | 3648 | 1467 | 106.7 | 73.44 | 31.67 | 53.86 | 71.45 | 27.32 | 37151 | 6983 | 255.5 | 110.9 |
| #16 | 1320 | 1382 | 183 | 206.3 | 18.72 | 20.91 | 79.95 | 78.79 | 32868 | 38041 | 202.2 | 321.1 |
| #17 | 1180 | 1207 | 192.8 | 187.1 | 24.11 | 21.3 | 64.8 | 64.09 | 35717 | 37394 | 273.6 | 287.6 |
| #26 | 1761 | 1549 | 210.7 | 205.2 | 20.76 | 22.14 | 88 | 62.51 | 33983 | 32628 | 290 | 287.6 |
| #29 | 1126 | 1803 | 210.8 | 206.2 | 21.18 | 24.01 | 112.9 | 108.7 | 34745 | 39326 | 290.5 | 317.2 |

Note:
in the table, "before" represented before stress, and "after" represented after stress.

As shown in Table 18 and FIGS. 17A-17F, interfering with MfERF026 enhanced the antioxidant capacity of the antioxidant enzyme system of transgenic *M. sativa*, including increasing the activities of SOD and POD and increasing the content of CAT, thereby making the H$_2$O$_2$ content significantly lower than that of the wild-type before and after stress.

(4) Cold Tolerance Test of Transgenic Lines with Inhibited Expression

The wild-type plants and transgenic lines #26 and #29 grown for 30 d in a soil matrix with vermiculite and nutrient soil at a volume ratio of 3:2 were treated in a low-temperature incubator, where the incubation program was: 0° C. 1 h, −1° C. 1 h, −2° C. 1 h, −3° C. 1 h, −4° C. 1 h, −5° C. 1 h, −6° C. 1 h, −7° C. 1 h, −8° C. 1 h, −9° C. 1 h, and then cultured overnight at 4° C. After −4° C. 1 h, some plants were taken out and immediately placed in a 4° C. plant incubator for overnight cultivation. Every time the temperature dropped by one degree centigrade, part of the plant material was taken out and immediately placed in a 4° C. plant incubator for overnight cultivation. The next day, all plant materials were placed at room temperature and recovered for 3 d. After 3 d of recovery, the survival rates of *M. sativa* in the experimental group and the control group were calculated. The changes in electric conductivity of *M. sativa* in the experimental group and the control group were detected and compared before and after the experiment. The CK control group was cultured at room temperature under the same experimental conditions. The calculation method of the electric conductivity was the same as that in (3).

Figure 18:
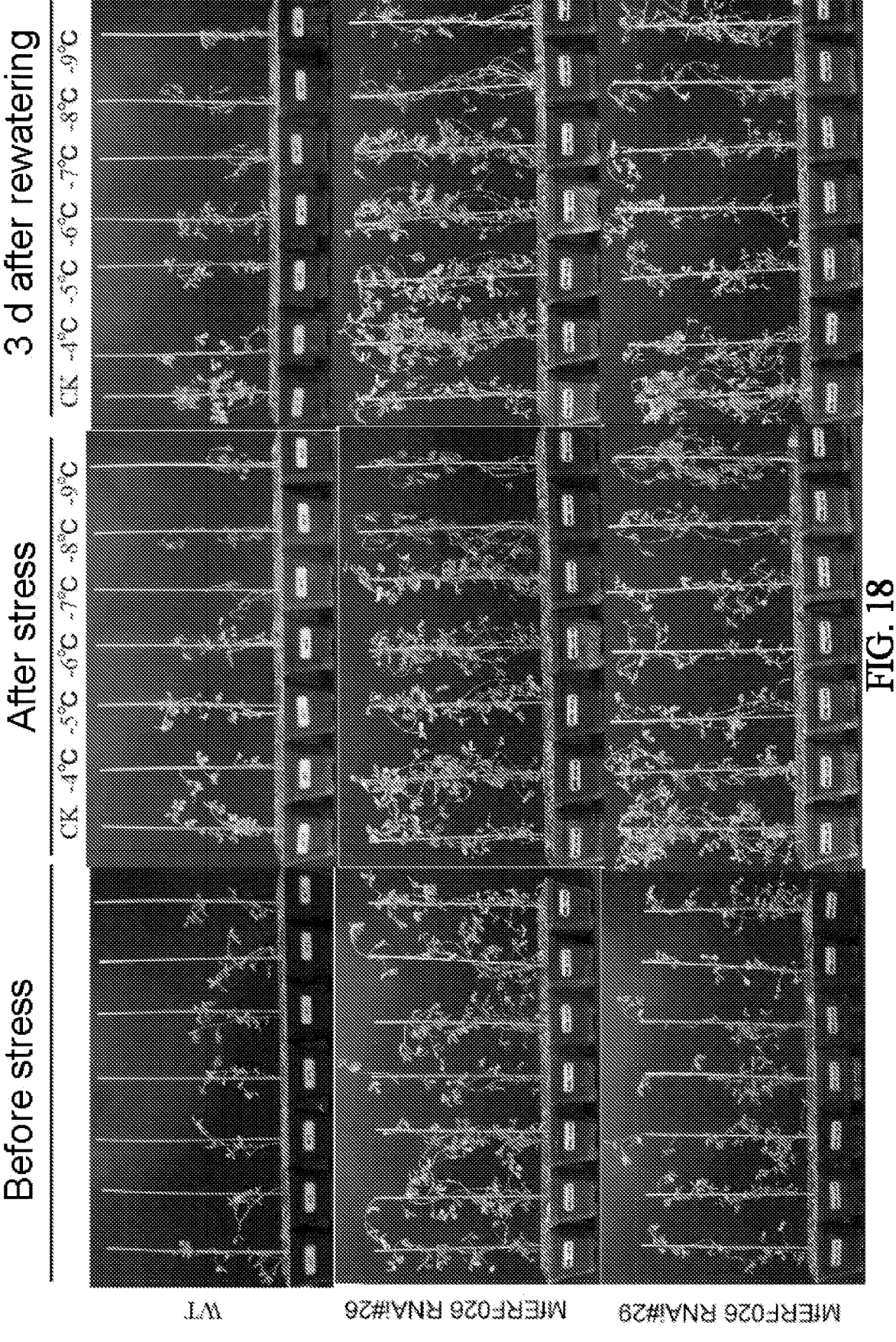
FIG. 18 shows the growth of plants during a cold tolerance test of the wild-type and transgenic lines.
Figure 19:
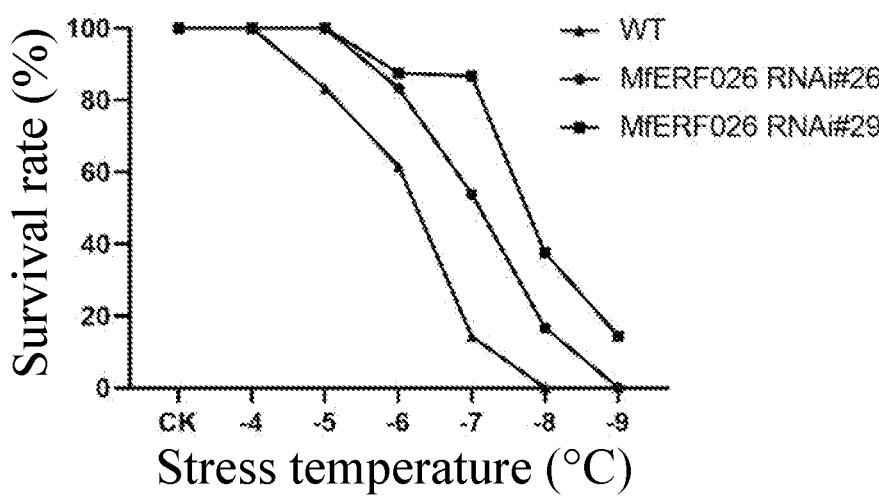
FIG. 19 shows the survival rates of the cold tolerance test of the wild-type and transgenic lines.
Figure 20:
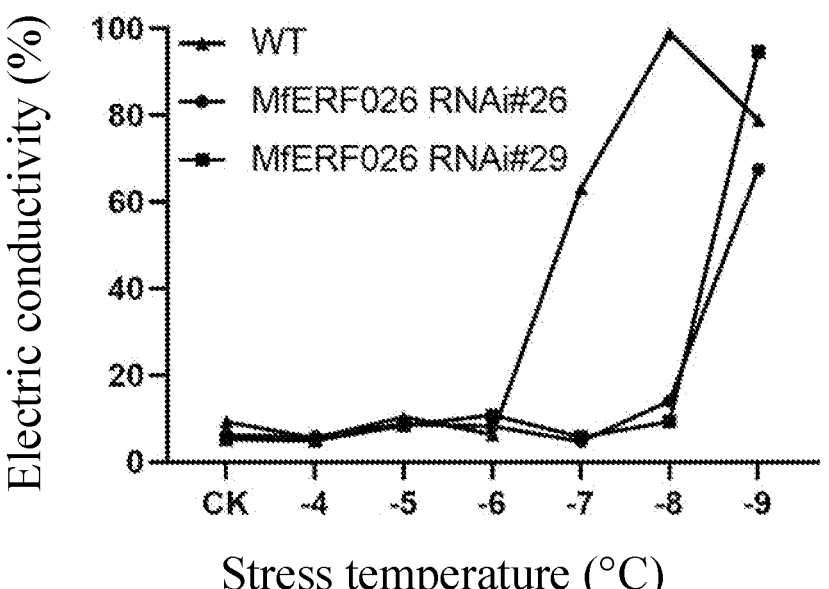
FIG. 20 shows the detection results of the electrical conductivity of the cold tolerance test of the wild-type and transgenic lines.

FIG. 18 shows the growth of plants during the cold tolerance test of the wild-type and transgenic lines. Table 19 and FIG. 19 show the survival rates of the cold tolerance test of wild-type and transgenic lines. Table 20 and FIG. 20 show the detection results of the electrical conductivity of the cold tolerance test of the wild-type and transgenic lines.

TABLE 19

Survival rates of cold tolerance test of wild-type and transgenic lines

| Survival rate | CK | −4 | −5 | −6 | −7 | −8 | −9 |
|---|---|---|---|---|---|---|---|
| WT | 100% | 100% | 83.33% | 61.54% | 14.29% | 0% | 0% |
| MfERF026 RNAi#26 | 100% | 100% | 100% | 83.33% | 53.85% | 16.67% | 0% |

TABLE 19-continued

Survival rates of cold tolerance test of wild-type and transgenic lines

| Survival rate | CK | −4 | −5 | −6 | −7 | −8 | −9 |
|---|---|---|---|---|---|---|---|
| MfERF026 RNAi#29 | 100% | 100% | 100% | 87.50% | 86.67% | 37.50% | 14.29% |

TABLE 20

Detection results of electrical conductivity of cold tolerance test of wild-type and transgenic lines

| Survival rate | CK | −4 | −5 | −6 | −7 | −8 | −9 |
|---|---|---|---|---|---|---|---|
| WT | 9.23% | 5.50% | 10.34% | 6.31% | 63% | 98.91% | 78.91% |
| MfERF026 RNAi#26 | 6.14% | 5.79% | 8.83% | 8.17% | 4.72% | 14.00% | 67.51% |
| MfERF026 RNAi#29 | 5.25% | 4.99% | 8.41% | 10.82% | 5.74% | 9.32% | 94.65% |

As shown in Tables 19 and 20 and FIG. 18 and FIG. 19, compared with wild-type WT, the MfERF026 transgenic line with inhibited expression had a higher survival rate under cold stress at −5° C. to −8° C. As shown in Table 20 and FIG. 20, the MfERF026 transgenic line with inhibited expression had a lower electrical conductivity, more complete cell membrane permeability, and lower degree of damage under cold stress at −7° C. and −8° C. These results indicated that transgenic plants showed better cold tolerance after inhibited expression of MfERF026.

In summary, the inhibited expression of the ERF MfERF026 in *M. falcata* provided by the present disclosure in the *M. sativa* may increase the drought tolerance and cold tolerance of *M. sativa*, and promote the growth and development of *M. sativa*, thereby increasing the growth rate and/or increasing the number of leaves for *M. sativa*.

Although the above examples have described the present disclosure in detail, it is only a part of, not all of the embodiments of the present disclosure. Other embodiments may also be obtained by persons based on the example without creative efforts, and all of these embodiments shall fall within the protection scope of the present disclosure.

What is claimed is:

1. A method for increasing plant height, number of tillers and number of trifoliate leaves of *Medicago sativa* (*M. sativa*), comprising infecting a *M. sativa* leaf with an engineered bacterium comprising an interfering RNA for an expression of MfERF026 to obtain a transformed *M. sativa* leaf; and subjecting the transformed *M. sativa* leaf to tissue culture to obtain a transgenic *M. sativa* with reduced MfERF026 expression, wherein MfERF026 encodes a protein having the amino acid sequence of SEQ ID NO: 2.

2. The method according to claim 1, wherein MfERF026 has the nucleotide sequence of SEQ ID NO: 1.

3. The method according to claim 1, wherein the interfering RNA silences or reduces the expression of MfERF026.

4. A trans-acting small interfering RNA (tasiRNA), wherein the tasiRNA has the nucleotide sequence of SEQ ID NO: 18.

5. A base fragment for reducing MfERF026 expression comprising the tasiRNA according to claim 4, wherein an expression vector comprises the base fragment having the nucleotide sequence of SEQ ID NO: 17.

6. A primer pair for amplifying the base fragment according to claim 5, wherein the primer pair comprises an upstream primer MfERF026 RNAi-F and a downstream primer MfERF026 RNAi-R; the upstream primer MfERF026 RNAi-F having a nucleotide sequence of SEQ ID NO: 14; and the downstream primer MfERF026 RNAi-R having the nucleotide sequence of SEQ ID NO: 15.

7. An engineered bacterium comprising the expression vector according to claim 5.

8. A method for constructing transgenic *M. sativa*, comprising:

infecting a *M. sativa* leaf with the engineered bacterium according to claim 7 to obtain a transformed *M. sativa* leaf; and subjecting the transformed *M. sativa* leaf to tissue culture to obtain the transgenic *M. sativa* with reduced MfERF026 expression.

*     *     *     *     *

```
                            SEQUENCE LISTING

Sequence total quantity: 20
SEQ ID NO: 1              moltype = DNA   length = 573
FEATURE                  Location/Qualifiers
source                   1..573
                         mol_type = other DNA
                         note = Medicago falcata
                         organism = Medicago sp.
CDS                      1..573
                         gene = MfERF026
                         protein_id = 2
                         translation = MNSSTIEQPHNSETKSSSNSSPPPPPSQSLQIKGIRDTSKHPVYRG
                          VRMRNWGKWVSEIREPKKKSRIWLGTFPTPEMAARAHDVAALSIKGSAAILNFPELVNL
                          LPRPASLAPRDIQAAATKAAHMEFPSSTASYELTEIIELPRLGNVGDFGKEFVFMDSID
                          TSWMFQPPCLQTMEDAIWSDIYNNYS
SEQUENCE: 1
atgaatagta gtactattga acaacctcat aactcagaaa ccaagagtag ctcaaattca  60
tcaccaccac caccaccatc acaatcccta caaataaaag gcataagaga cacaagcaag  120
catccagtat accgtggtgt ccgaatgcga aattggggaa aatgggtgtc cgaaattcgt  180
gagcctaaga aaaaatcccg aatatggctc ggcacatttc ccacaccaga aatggcagct  240
cgagcacacg atgtagctgc tcttagtata aaaggaagcg ccgccattct caacttccct  300
gagttagtaa acttgcttcc tcgtccggct tcactcgctc cccgtgatat tcaagcagcc  360
gctaccaaag ccgctcacat ggagtttcca tcttcaacag cttcatatga attgactgag  420
ataattgagc ttcctcgttt gggaaacgtt ggagattttg gaaaggagtt tgtatttatg  480
gattccattg atacttcgtg gatgtttcag cctccttgct tgcaaaccat ggaagatgcg  540
atttggagtg acatttataa taactatagc tag                              573

SEQ ID NO: 2              moltype = AA   length = 190
FEATURE                  Location/Qualifiers
source                   1..190
                         mol_type = protein
                         note = protein encoded by MfERF026
                         note = Medicago falcata
                         organism = Medicago sp.
SEQUENCE: 2
MNSSTIEQPH NSETKSSSNS SPPPPPSQSL QIKGIRDTSK HPVYRGVRMR NWGKWVSEIR  60
EPKKKSRIWL GTFPTPEMAA RAHDVAALSI KGSAAILNFP ELVNLLPRPA SLAPRDIQAA  120
ATKAAHMEFP SSTASYELTE IIELPRLGNV GDFGKEFVFM DSIDTSWMFQ PPCLQTMEDA  180
IWSDIYNNYS                                                         190

SEQ ID NO: 3              moltype = DNA   length = 20
FEATURE                  Location/Qualifiers
source                   1..20
                         mol_type = other DNA
                         note = Primer MfERFO26-F
                         organism = synthetic construct
SEQUENCE: 3
tttatttctc tccttcccat                                              20
```

-continued

```
SEQ ID NO: 4            moltype = DNA   length = 21
FEATURE                 Location/Qualifiers
source                  1..21
                        mol_type = other DNA
                        note = Primer MfERFO26-R
                        organism = synthetic construct
SEQUENCE: 4
aaacacacta agacattcac a                                              21

SEQ ID NO: 5            moltype = DNA   length = 20
FEATURE                 Location/Qualifiers
source                  1..20
                        mol_type = other DNA
                        note = Primer MfERF026DL-F
                        organism = synthetic construct
SEQUENCE: 5
attcaagcag ccgctaccaa                                                20

SEQ ID NO: 6            moltype = DNA   length = 20
FEATURE                 Location/Qualifiers
source                  1..20
                        mol_type = other DNA
                        note = Primer MfERF026DL-R
                        organism = synthetic construct
SEQUENCE: 6
cctttccaaa atctccaacg                                                20

SEQ ID NO: 7            moltype = DNA   length = 41
FEATURE                 Location/Qualifiers
source                  1..41
                        mol_type = other DNA
                        note = Primer MfERF026 PBE-F
                        organism = synthetic construct
SEQUENCE: 7
gactctagag cagtcgacga tgaatagtag tactattgaa c                        41

SEQ ID NO: 8            moltype = DNA   length = 41
FEATURE                 Location/Qualifiers
source                  1..41
                        mol_type = other DNA
                        note = Primer MfERF026 PBE-R
                        organism = synthetic construct
SEQUENCE: 8
ggcgaccggt ggatcccggc tatagttatt ataaatgtca c                        41

SEQ ID NO: 9            moltype = DNA   length = 30
FEATURE                 Location/Qualifiers
source                  1..30
                        mol_type = other DNA
                        note = Primer MfERF026a-F
                        organism = synthetic construct
SEQUENCE: 9
cgggatccat gaatagtagt actattgaac                                     30

SEQ ID NO: 10           moltype = DNA   length = 38
FEATURE                 Location/Qualifiers
source                  1..38
                        mol_type = other DNA
                        note = Primer MfERF026a-R
                        organism = synthetic construct
SEQUENCE: 10
ataagaatgc ggccgcctag ctatagttat tataaatg                            38

SEQ ID NO: 11           moltype = DNA   length = 36
FEATURE                 Location/Qualifiers
source                  1..36
                        mol_type = other DNA
                        note = Primer MfERF026b-R
                        organism = synthetic construct
SEQUENCE: 11
ataagaatgc ggccgcaagc aagtttacta actcag                              36

SEQ ID NO: 12           moltype = DNA   length = 25
FEATURE                 Location/Qualifiers
source                  1..25
                        mol_type = other DNA
                        note = Primer MfERF026c-F
                        organism = synthetic construct
SEQUENCE: 12
```

-continued

```
cgggatccgt ataccgtggt gtccg                                         25

SEQ ID NO: 13           moltype = DNA   length = 26
FEATURE                 Location/Qualifiers
source                  1..26
                        mol_type = other DNA
                        note = Primer MfERF026e-F
                        organism = synthetic construct
SEQUENCE: 13
cgggatcccc tcgtccggct tcactc                                        26

SEQ ID NO: 14           moltype = DNA   length = 50
FEATURE                 Location/Qualifiers
source                  1..50
                        mol_type = other DNA
                        note = Primer MfERF026 RNAi-F
                        organism = synthetic construct
SEQUENCE: 14
cgggatcctt cagaggtgaa gacacacgta gatgtagctg ctcttagtat             50

SEQ ID NO: 15           moltype = DNA   length = 30
FEATURE                 Location/Qualifiers
source                  1..30
                        mol_type = other DNA
                        note = Primer MfERF026 RNAi-R
                        organism = synthetic construct
SEQUENCE: 15
gctctagact agctatagtt attataaatg                                    30

SEQ ID NO: 16           moltype = DNA   length = 24
FEATURE                 Location/Qualifiers
source                  1..24
                        mol_type = other DNA
                        note = Primer 3xFlag-R
                        organism = synthetic construct
SEQUENCE: 16
ctacttatcg tcatcgtcct tgta                                          24

SEQ ID NO: 17           moltype = DNA   length = 362
FEATURE                 Location/Qualifiers
source                  1..362
                        mol_type = other DNA
                        note = Base fragment for reducing MfERF026 expression
                        organism = synthetic construct
SEQUENCE: 17
cgggatcctt cagaggtgaa gacacacgta gatgtagctg ctcttagtat aaaaggaagc  60
gccgccattc tcaacttccc tgagttagta aacttgcttc ctcgtccggc ttcactcgct  120
ccccgtgata ttcaagcagc cgctaccaaa gccgctcaca tggagtttcc atcttcaaca  180
gcttcatatg aattgactga gataattgag cttcctcgtt tgggaaacgt tggagatttt  240
ggaaaggagt ttgtatttat ggattccatt gatacttcgt ggatgtttca gcctccttgc  300
ttgcaaacca tggaagatgc gatttggagt gacatttata ataactatag ctagtctaga  360
gc                                                                  362

SEQ ID NO: 18           moltype = RNA   length = 22
FEATURE                 Location/Qualifiers
source                  1..22
                        mol_type = other RNA
                        note = tasiRNA
                        organism = synthetic construct
SEQUENCE: 18
ttcagaggtg aagacacacg ta                                            22

SEQ ID NO: 19           moltype = DNA   length = 21
FEATURE                 Location/Qualifiers
source                  1..21
                        mol_type = other DNA
                        note = Primer Actin-F
                        organism = synthetic construct
SEQUENCE: 19
gctgatagga tgagcaagga g                                             21

SEQ ID NO: 20           moltype = DNA   length = 25
FEATURE                 Location/Qualifiers
source                  1..25
                        mol_type = other DNA
                        note = Primer Actin-R
                        organism = synthetic construct
```

-continued

SEQUENCE: 20
gagcctccaa tccagcagac actat                                    25